US008649982B2

(12) United States Patent
Woo et al.

(10) Patent No.: US 8,649,982 B2
(45) Date of Patent: *Feb. 11, 2014

(54) AUTOMATIC THRESHOLD SETTING AND BASELINE DETERMINATION FOR REAL-TIME PCR

(75) Inventors: David Woo, Foster City, CA (US); Clinton Lewis, Palo Alto, CA (US); Nasser Abbasi, San Mateo, CA (US)

(73) Assignee: Applied Biosystems, LLC, Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/231,618

(22) Filed: Sep. 13, 2011

(65) Prior Publication Data

US 2012/0072120 A1 Mar. 22, 2012

Related U.S. Application Data

(63) Continuation of application No. 11/645,964, filed on Dec. 27, 2006, now Pat. No. 8,036,832, which is a continuation of application No. 10/152,280, filed on May 20, 2002, now Pat. No. 7,228,237.

(60) Provisional application No. 60/355,661, filed on Feb. 7, 2002.

(51) Int. Cl.
*G01N 33/48* (2006.01)

(52) U.S. Cl.
USPC .......................................................... 702/19

(58) Field of Classification Search
USPC .......................................................... 702/19
See application file for complete search history.

(56) References Cited

U.S. PATENT DOCUMENTS

| | | | |
|---|---|---|---|
| 5,710,381 A | 1/1998 | Atwood et al. | |
| 6,174,670 B1 | 1/2001 | Wittwer et al. | |
| 6,303,305 B1 | 10/2001 | Wittwer et al. | |
| 6,763,934 B2 | 7/2004 | Nakamura | |
| 6,783,934 B1 | 8/2004 | McMillan et al. | |
| 6,911,327 B2 | 6/2005 | McMillan et al. | |
| 7,363,168 B2 | 4/2008 | Taylor et al. | |
| 2002/0009394 A1 | 1/2002 | Koster et al. | |
| 2002/0031768 A1 | 3/2002 | McMillan et al. | |
| 2002/0116135 A1 | 8/2002 | Pasika et al. | |
| 2003/0148332 A1 | 8/2003 | Taylor et al. | |

FOREIGN PATENT DOCUMENTS

| | | |
|---|---|---|
| EP | 1041158 | 10/2000 |
| EP | 1138783 | 10/2001 |

OTHER PUBLICATIONS

Alexandersen, et al., The Early Pathogenesis of Foot-and-Mouth Disease in Pigs Infected by Contact: A Quantitative Time-Course Study Using TaqMan RT-PCR, Gen Virol., vol. 82, (pt 4), pp. 747-755 (Abstract) (2001).
Applied Biosystems, User Bulletin #2, ABI Prism 7700 Sequence Detection System, Setting Baseline and Thresholds, pp. 1-12 (2002).
Bustin, et al., Absolute Quantification of mRNA Using Real-Time Reverse Transcription Polymerase Chain Reaction Assays, Journal of Molecular Endocrinology, vol. 25, pp. 169-193 (2000).
Bustin, et al., Quantification of mRNA Using Real-Time Reverse Transcription PCR (RT-PCR): Trends and Problems, Journal of Molecular Endocrinology, vol. 29, pp. 23-39 (2002).
Diaz, et al., Chapter 16: Algebraic Algorithms in Algorithms and Theory of Computation Handbook, Ed. Mikhail J. Atallah, CRC Press 1998.
Freeman, et al., Quantitative RT-PCR: Pitfalls and Potential, BioTechniques, vol. 26, No. 1, pp. 112-125 (1999).
Ginzinger, et al., Gene Quantification Using Real-Time Quantitative PCR: An Emerging Technology Hits the Mainstream, Elsevier Science Inc., Experimental Hematology, vol. 30, pp. 503-512, (2002).
Giulietti, et al., An Overview of Real-Time Quantitative PCR: Applications to Quantify Cytokine Gene Expression, Methods, vol. 25, pp. 386-401, Elsevier Science (USA) (2001).
Grove, et al., Quantitative Real-Time Polymerase Chain Reaction for the Core Facility Using TaqMan and the Perkin-Elmer/Applied Biosystems Division 7700 Sequence Detector, ABRF pp. 1-11 (1999).
Haake, et al., "Label-Free Biochemical Detection Coupled On-Line to Liquid Chromatography," Analytical Chemistry, 2000, vol. 72, pp. 3635-3641.
Heid, et al., "Real Time Quantitative PCR", Genome Research, Cold Spring Harbor Laboratory Press, Woodbury, NY, vol. 6 (10), vol. 6, Issue 10, pp. 986-994 (1996).
Higuchi, R., et al., "Kinetic PCR Analysis: Real-Time Monitoring of DNA Amplification Reactions", BioTechnology, vol. 11, 1993, 1026-1030.
Levis, et al., Strategy for the Maximization of Clinically Relevant Information from Hepatitis C Virus, RT-PCT Quantification, J. Clin. Virol, vol. 20, No. 3, pp. 163-171 (2001).
Lie, Y, et al., "Advances in Quantitative PCR Technology: 5' nuclease assays", Analytical Biotechnology, vol. 14, 303-308 (1998).
Livak, et al., Analysis of Relative Gene Expression Data Using Real-Time Quantitative PCR and the $2^{-DDC}{}_T$ Method, Methods, vol. 25, pp. 402-408 (2001).
Marchand, et al., Review of Scientific Instuments, 1983, vol. 54, Issue 8, pp. 1034-1041.
Module, et al., Webster's Third New International Dictionary, Unabridged, 1993.
Morin, et al., Laboratory for Conservation Genetics, Leipzig, Molecular Ecology, vol. 10, pp. 1835-1844, www.rareDNA.com (2001).
Morrison, et al., Nanoliter High Throughput Quantitative PCR, Nucleic Acids Research, vol. 34, No. 18, pp. 1-9 and e 123 (2006).
Morrison, et al., Nanoliter High Throughput Quantitative PCR, Nucleic Acids Research, vol. 34. No. 18, e123, pp. 1-9 and e 123 (2006).

(Continued)

*Primary Examiner* — Jerry Lin

(57) ABSTRACT

The invention discloses a system and methods for quantitating the presence of nucleic acid sequences by evaluation of amplification data generated using real-time PCR. In one aspect, the methods may be adapted to identify a threshold and threshold cycle for one or more reactions based upon evaluation of exponential and baseline regions for each amplification reaction. The methodology used in the analysis may be readily automated such that subjective user interpretation of the data is substantially reduced or eliminated.

14 Claims, 15 Drawing Sheets

(56) References Cited

OTHER PUBLICATIONS

Nitsche, et al., Different Real-Time PCR Formats Compared for the Quantitative Detection of Human Cytomegalovirus DNA, Clinical Chemistry, 45:11, 1932-1937 (1999).

Pfaffl, et al., New Mathematical Model for Relative Quantification in Real-Time RT-PCR, Nucleic Acids Research, vol. 29, No. 9, p. e 45 (2001).

Rasmussen, et al., Quantitative PCR by Continuous Fluorescence Monitoring of a Double Strand DNA Specific Binding Dye, Biochemica, No. 2, pp. 8-11 (1998).

Roche Molecular Biochemicals: Lightcycler Absolute Quantification with External Standards, Technical Note No. LC, Nov. 2000.

Roche Molecular Biochemicals: Lightcycler Operator's Manual, http://biochem.roche.com/lightcycler, Version 3.5: Prologue, Oct. 2000, 1-189.

Roche Molecular Biochemicals: Lightcycler Relative Quantification Software, Version 1, Mar. 2001.

Rostaing, et al., Changes in Hepatitis C Virus RNA Viremia Concentrations in Long-Term Renal Transplant Patients after Introduction of Mycophenolate Mofetil, Transplantation, vol. 15, No. 69(5), pp. 991-994 (Abstract) (2000).

Saraswathy, et al., Human Immunodeficiency Virus Type 1 Subtypes Among Malaysian Intravenous Drug Users, Southeast Asian J. Trop. Med. Public Health (Abstract), vol. 31, No. 2, pp. 283-286 (2000).

Winer, et al., Development and Validation of Real-Time Quantitative Reverse Transcriptase-Polymerase Chain Reaction for Monitoring Gene Expression in Cardiac Myocytes in Vitro, Analytical BioChemistry, vol. 270, No. 1, pp. 41-49, May 1999.

Woudenberg, et al., Quantitative PCR by real-time detection, Proc. of SPIE, vol. 2680, 1996, 306-315.

Yajima, et al., Quantitative Reverse Transcription—PCR Assay of the RNA Component of Human Telomerase Using the TaqMan Fluorogenic Detection System, Clinical Chemistry 44:12, pp. 2441-2445 (1998).

AUTOMATIC THRESHOLD SETTING AND BASELINE DETERMINATION FOR REAL-TIME PCR

CROSS-REFERENCE TO RELATED APPLICATION

The present application is a continuation of U.S. patent application Ser. No. 11/645,964 filed on Dec. 27,2006 now U.S. Pat. No. 8,036,832, which is a continuation of U.S. patent application Ser. No. 10/152,280, filed May 20, 2002 now U.S. Pat. No. 7,228,237, which claims priority to U.S. Provisional Patent Application No. 60/355,661, entitled "Automatic Threshold Setting And Baseline Determination For Quantitative PCR" filed Feb. 7, 2002, all of which are hereby incorporated by reference.

BACKGROUND

The invention generally relates to nucleic acid analysis, and more particularly, to a system and methods for evaluating results obtained from quantitative amplification reactions.

DESCRIPTION OF THE RELATED ART

Quantitative nucleic acid analysis is extensively used in biological research and clinical analysis. Some of the applications which make use of this technology include: measurement of gene expression, monitoring of biological responses to stimuli, genomic-level gene quantitation, and pathogen detection. Typically, these methodologies utilize Polymerase Chain Reaction (PCR) as a means for selectively amplifying nucleic acid sequences in a manner that allows for their detection. While it is generally desirable to automate the quantitation process, conventional methodologies often require a degree of user input in the form of subjective interpretation and/or approximation. As a result, these techniques may suffer from reduced accuracy and significant user-induced variability. Furthermore, in high-throughput applications where many samples are to be processed simultaneously, it is desirable to provide increased automation capabilities to improve the speed with which the analysis may be conducted. The aforementioned limitations of conventional techniques illustrate the need for an improved method for analyzing data generated by PCR-based quantitation techniques that may increase the potential for automation while improving the quantitative accuracy and reproducibility of the analysis.

SUMMARY

In one embodiment, the invention comprises a system and methods for processing and evaluating data generated in real-time quantitative PCR. During the amplification reaction, fluorescence intensity signals are acquired that form an amplification profile from which an exponential amplification region is desirably identified. In determining the exponential region, the invention determines the upper and lower bounds where more efficient amplification takes place and identifies a baseline used to estimate and compensate for noise. Subsequently, a threshold and threshold cycle are determined which may be used to quantitate the initial target concentration present at the onset of the amplification reaction.

In another embodiment, the invention comprises a method for quantifying nucleic acid sequences present in one or more amplification reactions to be collectively analyzed. The method further comprising the steps of: (a) acquiring intensity data for each reaction over a selected number of reaction intervals wherein the intensity data is indicative of a detected quantity of progeny sequences arising from each sequence; (b) assessing the intensity data over the selected number of reaction intervals to generate an amplification profile indicative of the change in quantity of the progeny sequences for each reaction interval; (c) evaluating each amplification profile to identify a corresponding exponential region, having upper and lower bounds; (d) determining a threshold based upon an intersection between at least one exponential region upper bound with at least one exponential region lower bound; (e) performing a polynomial fitting operation for each amplification profile that applies the threshold to determine a polynomial root which is thereafter associated with a threshold cycle for each reaction; and (f) quantifying the sequence for each reaction using the threshold cycle.

In still another embodiment, the invention comprises a method for quantitating at least one nucleic acid target of unknown concentration. The method further comprising the steps of: (a) performing PCR-based amplification of each target using a detectable reporter construct; (b) acquiring detection information generated by the detectable reporter construct indicative of a change in the concentration of each target over the course of the amplification; (c) assembling a data set comprising at least a portion of the detection information to model amplification reaction characteristics; (d) identifying an exponential region for each target of the data set from the modeled amplification reaction characteristics; (e) identifying a baseline component based, in part, on the exponential region; (f) normalizing the data set using the baseline component; (g) determining a threshold based upon a comparison of the exponential regions for the targets of the data set; (h) identifying a polynomial equation whose root is identified using the threshold and wherein the root is assigned as a threshold cycle; and (i) quantifying each target using the threshold cycle.

In a still another embodiment, the invention comprises a system for analyzing quantitative amplification data. The system further comprises a reaction module, a data collection module, and a data processing module wherein: The reaction module used to perform PCR amplification of at least one sample target using a detectable reporter label; The data collection module that detects reporter label intensities over the course of the PCR amplification for the at least one sample target; The data processing module configured to: (a) receive the detected intensities for each sample target and subsequently generate a corresponding amplification profile to model the PCR amplification for the sample target; (b) identify an exponential region for each amplification profile, each exponential region further having upper and lower bounds; (c) identify a characteristic equation for each amplification profile based, in part, from the lower bound of the exponential threshold, and thereafter generate a normalized amplification profile using the characteristic equation; and (d) identify a threshold and threshold cycle using the normalized amplification profile.

BRIEF DESCRIPTION OF THE DRAWINGS

These and other aspects, advantages, and novel features of the invention will become apparent upon reading the following detailed description and upon reference to the accompanying drawings. In the drawings, similar elements have similar reference numerals.

DETAILED DESCRIPTION OF THE CERTAIN EMBODIMENTS

Figure 1:
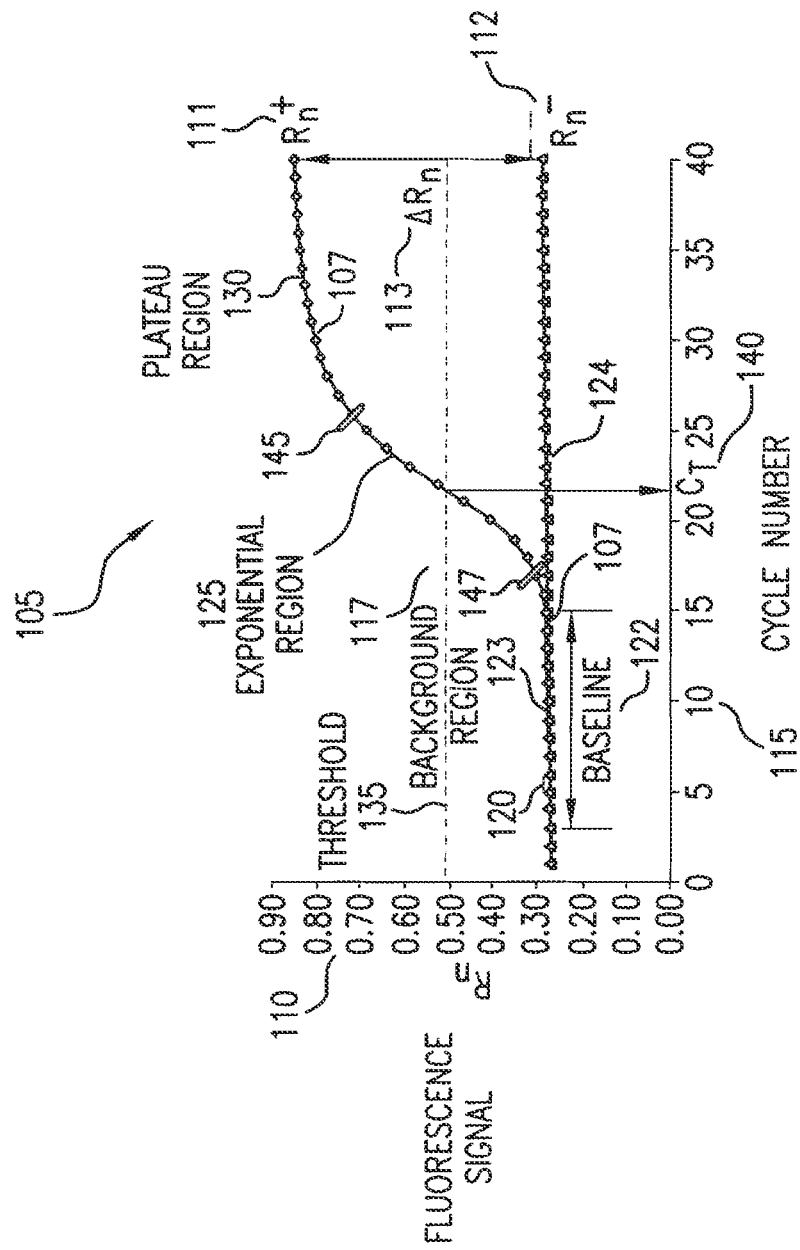
FIG. 1 illustrates an exemplary amplification plot for a quantitative PCR reaction.

Reference will now be made to the drawings wherein like numerals refer to like elements throughout. As used herein, "target", "target polynucleotide", and "target sequence" and the like refer to a specific polynucleotide sequence that is the subject of hybridization with a complementary polynucleotide, e.g., a blocking oligomer, or a cDNA first strand synthesis primer. The target sequence can be composed of DNA, RNA, analogs thereof, or combinations thereof. The target can be single-stranded or double-stranded. In primer extension processes, the target polynucleotide which forms a hybridization duplex with the primer may also be referred to as a "template." A template serves as a pattern for the synthesis of a complementary polynucleotide (Concise Dictionary of Biomedicine and Molecular Biology, (1996) CPL Scientific Publishing Services, CRC Press, Newbury, UK). A target sequence for use with the present invention may be derived from any living or once living organism, including but not limited to prokaryote, eukaryote, plant, animal, and virus, as well as synthetic and/or recombinant target sequences.

Furthermore, in describing the invention, as used herein the polynucleotide sequence may refer to a polynucleotide chain of variable length and may comprise RNA. DNA, cRNA, cDNA, or other polynucleotide species including but not limited to analogs having other than a phosphodiester backbone. Furthermore, as used herein, "reaction interval" refers to a designated portion of a target amplification reaction and may be evaluated as a function of cycle number or reaction time. Additionally, as used herein, "intensity data" refers to a measured or observed signal generated during the amplification reaction which may be related to the amount of target in the reaction and may comprise fluorescent measurements, radiolabel measurements, electrical measurements, light emission measurements, and other types of signals and measurements generated and acquired during the amplification reaction.

In general, amplification of a target DNA strand by polymerase chain reaction (PCR) proceeds through a series of temperature regulated cycles using the activity of a thermostable enzyme and a sequence specific primer set. At an appropriate temperature, primers hybridize to portions of the DNA strand and the enzyme successively adds a plurality of nucleotide bases to elongate the primer resulting in the production of progeny (daughter) strands. Each progeny strand possesses a complimentary composition relative to the target strand from which it was derived and can serve as a target in subsequent reaction cycles.

When applying quantitative methods to PCR-based technologies, a fluorescent probe or other detectable reporter construct may be incorporated into the reaction to provide a means for determining the progress of the target amplification. In the case of a fluorescent probe, the reaction can be made to fluoresce in relative proportion to the quantity of nucleic acid product produced. The TAQMAN® fluorescent probe procedure (Applied Biosystems, Calif.) describes one such fluorescent methodology for performing quantitative PCR.

Briefly described, the TAQMAN® system integrates the use of a detectable reporter construct which comprises both a fluorescent label molecule and a quencher molecule. As long as the reporter construct remains intact, fluorescent label molecule emissions are absorbed by the quencher molecule. During the amplification process, however, the reporter construct is cleaved and the quencher molecule is released allowing the fluorescent label molecule emissions to be detected. The quantity or intensity of observed fluorescence may then be correlated with the amount of product formed throughout the reaction. Using this information, the initial quantity of target present in the reaction may be determined. Additional information describing the principles and applications of quantitative PCR can be found in: *Real Time Quantitative PCR*, Genome Research, Cold Spring Harbor Laboratory Press, 1996 and *PCR Technology: Principles and Applications for DNA Amplification*. Karl Drlica, John Wiley and Sons, 1997.

One characteristic feature of quantitative PCR-based amplification is that, the reaction kinetics typically change over the course of the reaction with the amount of product formed not necessarily increasing in a constant manner. For example, during the earlier cycles of a PCR reaction there may be an approximate doubling of the nucleotide strands with each cycle (exponential amplification). In the later cycles of the reaction, however, the efficiency of the amplification process may be diminished resulting in non-exponential amplification. Some of the factors that may affect the amplification efficiency include limiting quantities or depletion of reagents and competition for reaction products. The aforementioned changes in reaction kinetics may result in difficulties in determining the initial target concentration without performing detailed analysis of the reaction profile. In one aspect, it is desirable to monitor the reaction at various time or cycle intervals and acquire data which quantifies the emitted fluorescence of the reaction at these intervals. Using this information, data analysis methods may be used to assess the acquired fluorescence measurements and determine the initial concentration of target present in the reaction.

In quantitation methodologies, including real-time PCR, the fluorescence intensity for each amplification reaction may be determined using a charge-coupled device (i.e. CCD camera or detector) or other suitable instrument capable of detecting the emission spectra for the label molecules used in the reporter construct. Fluorescence samplings are performed over the course of the reaction and may be made at selected time intervals (for example: 25 millisecond samplings performed at 8.5-second intervals). In one aspect, emission spectra are measured for both the label molecule and the quencher molecule with the emission intensity resultant from the quencher molecule changing only slightly compared to that of the label molecule. The emission intensity of the quencher molecule may further be used as an internal standard to normalize emissions generated by the label molecule.

For each amplification reaction, the measured emission spectra obtained from the fluorescence samplings form an amplification data set that may be processed to determine the initial target concentration. In one aspect, the amplification data set comprises fluorescence intensity information obtained from a plurality of independent or coupled reactions. These reactions may be performed simultaneously or at different times wherein the data is accumulated and collectively analyzed. Furthermore, the amplification data set may further comprise fluorescence intensity data obtained from one or more standards whose initial target concentration is known.

As will be described in greater detail with reference to the Figures below, the methodologies presented herein may be applied to determine the concentration of target present in each reaction prior to amplification. It will be appreciated that while described in the context of PCR-based amplification reactions and data, the analysis procedures may be applied of other nucleic acid amplification methodologies such as Nucleic Acid Sequence Based Amplification (NASBA). Additionally, the target nucleotide sequence whose initial concentration is to be determined may comprise nucleic acid sequences including DNA, cDNA, RNA, cRNA or any combination thereof and may be present as single or double stranded nucleotide species. Furthermore, other types or configurations of reporter constructs may be similarly adapted for use with the methods described herein including radiolabeled and chemiluminescent constructs, as well as other labeling constructs that are detectable over the course of the amplification of the target.

FIG. 1 illustrates an amplification plot 105 depicting the reaction characteristics for an exemplary nucleic acid target and the various analytical components that may be used to quantify the target. It will be appreciated that the amplification plot 105 is shown for the purposes of explanation and need not necessarily be constructed directly to apply the quantitative methods of the invention. However, the system can be configured to present a graphical representation of the amplification data set to aid a user in visualizing the results of the analysis.

The amplification plot 105 comprises a plurality of data points 107 forming an amplification profile 117 which is indicative of the measured intensity of signal generated by the label molecules within the amplification reaction. In the amplification plot 105, the y-axis values 110 correspond to observed signal intensities generated over the course of the amplification reaction. In one aspect, these signal intensities may correspond to fluorescent emissions obtained from instrumental sampling using a charge-coupled device or similar apparatus. Furthermore, the fluorescence detector may be configured to monitor wavelengths from approximately 500 to 650 nm. The x-axis values 115 correspond to the sample interval (shown as a function of cycle number) for the amplification reaction for which the signals are observed. Illustrated in this manner, the information represents the reaction progression as a function of the observed fluorescence intensities over the sampling interval and may be used to monitor the synthesis of progeny nucleic acid strands from an initial sample target.

When analyzing the amplification profile 117 various regions may be desirably identified that are subsequently used in calculations for determining the initial concentration of target present in the reaction. A common limitation of conventional analysis methodologies is a requirement for at least a degree of subjective interpretation. Oftentimes, a user must visually inspect the intensity data from a data set in order to identify relevant regions of the amplification profile 117 which are to be used in subsequent quantitative analysis. This subjective manner of manual analysis is undesirable and may decrease the accuracy of the quantitation results, as well as, increase the analysis time.

In one aspect, the system and methods described herein overcome some of the limitations and drawbacks associated with conventional methodologies through the implementation of an analysis strategy that identifies significant regions of the amplification profile 117 in an objective and reproducible manner. As a result, the invention may improve the accuracy of quantification when determining the initial concentration of target present in an amplification reaction.

As shown by way of example in FIG. 1, the results from a typical quantitation reaction can be characterized by different regions 120, 125, 130 within, the amplification profile 117 corresponding to a baseline (noise) region 120, an exponential region 125, and a plateau region 130. During the earlier cycles of the reaction, the observed fluorescence produced by the label generally does not substantially exceed that produced by the quencher. Fluorescent emissions measured during these cycles are generally very low and may fall below the detection limits or sensitivity of the data acquisition instrumentation. Furthermore, within this region 120 non-specific florescence arising from instrumental variations or noise may significantly contribute to the observed signal. As a result, in the early cycles of the reaction it may be difficult to accurately determine the emission fluorescence arising from true products of amplification, which may not be readily distinguishable from background and/or non-specific fluorescence present during detection. It is therefore desirable to identify reaction fluorescence data in the background region 120 to avoid inaccuracies in quantitation which may arise if these values are inappropriately used to perform the analysis. Furthermore, during the quantitative analysis it may be desirable to identify the range and bounds of the background region 120 so that this portion of the amplification reaction may be distinguished from other regions of the amplification profile 117 where detected fluorescence may more accurately reflect the fluorescence of the desired products of the reaction.

In order to characterize the background region 120 for the purposes of analysis, a sub-region within the background region 120 may further be identified as a baseline data set 122. The baseline data set 122 serves as an indicator of the relative level of background fluorescence or noise from which the exponential region 125 may be differentiated. In one aspect, a linear regression analysis may be performed on the baseline data set 122 to identify a baseline 123 which can be described by a characteristic equation used to evaluate the amplification data. As will be described in greater detail herein below, construction of the baseline 123 provides a means to quantify the relative noise present in the amplification reaction. Furthermore, the baseline 123 may be used to normalize the data points 107 of the amplification profile 117 in order to at least partially compensate for the noise.

In order to normalize data points 107, which lie outside of the background region 120, the baseline 123 may be extended using the characteristic equation. In one aspect, the characteristic equation comprises a one-degree equation, which describes the baseline properties and can be extended to the terminal data point of the amplification reaction. The extended baseline 124 can therefore be configured to span substantially the entire amplification profile or a portion thereof to facilitate normalization of all data points 107 within the amplification profile 117. By taking the difference between the observed intensity ($R^+_n$) 111 of each data point 107 within the amplification profile 117 and the calculated intensity ($R^-_n$) 112 of the baseline 123 (or extended baseline 124) at the appropriate interval, a normalized intensity value ($\Delta R_n$) 113 may be obtained. Using this information, a normalized data set may be generated (data not shown), and used in subsequent quantitation of the target in a manner that will be discussed detail with reference to FIG. 4 below.

The exponential region 125 comprises a region of the amplification profile 117 following the background region 120 where data points 107 generally exhibit a trend of substantially increasing or progressive fluorescence. It is within this portion of the amplification profile 117 where the observed intensity of fluorescence generally better correlate with an exponentially increasing sample concentration with each cycle. Within the exponential region 125, the detected quantity of fluorescence is typically sufficient to overcome noise that may predominate in the background region 120. The characteristics of the amplification reaction during the cycles associated with the exponential region 125 further reflect desirable reaction kinetics that can be used to perform quantitative target calculations.

It will be appreciated that the increase in target concentration within the exponential region 125 need not necessarily follow a substantially exponential rate. Instead, this region 125 of the amplification profile 117 may be substantially characterized by a sub-exponential, geometric, linear and/or progressive rate of increase in target concentration. More generally, the amplification region 125 may be characterized as the portion of the amplification profile 117 where an increased rate of target accumulation may be observed relative to earlier and later cycles of the reaction. It will be appreciated that the methods described herein are suitable for assessing amplification reactions having a wide variety of characteristic increases in target concentration and are not limited exclusively to assessing regions of "pure" exponential increase.

In certain embodiments, an advantage of the present invention is the ability to evaluate the exponential region 125 in an automated manner. In one aspect, exponential region evaluation comprises determining an upper bound 145 and lower bound 147 which delineate the approximate limits of the exponential region 125. This information is subsequently used to identify the bounds of the baseline region 120, calculate the baseline 123, and extend baseline 124. Additional details of these methods will be described in greater detail in subsequent illustrations and discussion.

As shown in FIG. 1, the exponential region 125 may be followed by a plateau region 130 where the reaction ceases to increase in an exponential manner. Typically, the plateau region 130 occurs in the later cycles of the reaction as the amplification reaction transitions out of the exponential region 125. When performing quantitation calculations, it is useful to distinguish the exponential region 125 from the plateau region 130 to avoid erroneous or non-representative quantitation values. As with distinguishing the background region 120 from the exponential region 125, the methods described herein similarly distinguish the plateau region 130 from the exponential region 125 which may help to improve the quality of the resultant calculations that make use of this information.

Although the delineation of discrete regions within the amplification profile 117 is useful for distinguishing characteristic reaction kinetics and further identifying portions of the amplification profile amenable to quantitation calculations, it will be appreciated by one of skill in the art that specific designation of these regions is not required to perform the quantitative calculations described herein. It will further be appreciated that the characteristics of these regions may vary from one reaction to the next and may deviate significantly from illustrated profile. For example, in some amplification reactions, the exponential region 125 may extend over a different range of cycles and possess different intensity characteristics. Likewise, the background region 120 and the plateau region 130 may possess unique characteristics for each reaction. Additionally, other regions within the amplification profile 117 may be identifiable, for example, a region of substantial linearity may follow the exponential region 125. As will be described in greater detail herein below, the quantitation methods may be desirably "tuned" or customized to accommodate potentially diverse classes of amplification profile characteristics.

The analytical approach used to quantitate the initial target concentration is based, in part, upon the identification of a threshold 135. In one aspect, the threshold 135 desirably aids in identifying and delineating noise present in the background region 120 and furthermore intersects with the amplification profile 117 at some point. The point of intersection between the threshold 135 and the amplification profile 117 is identified by a threshold cycle 140 ($C_T$) which is representative of a cycle number associated with the point of intersection. As will be appreciated by one of skill in the art, identification of the threshold cycle 140 is desirable as this value may be used in subsequent calculations to predict the initial quantity or concentration of target present in the reaction.

Figure 2:
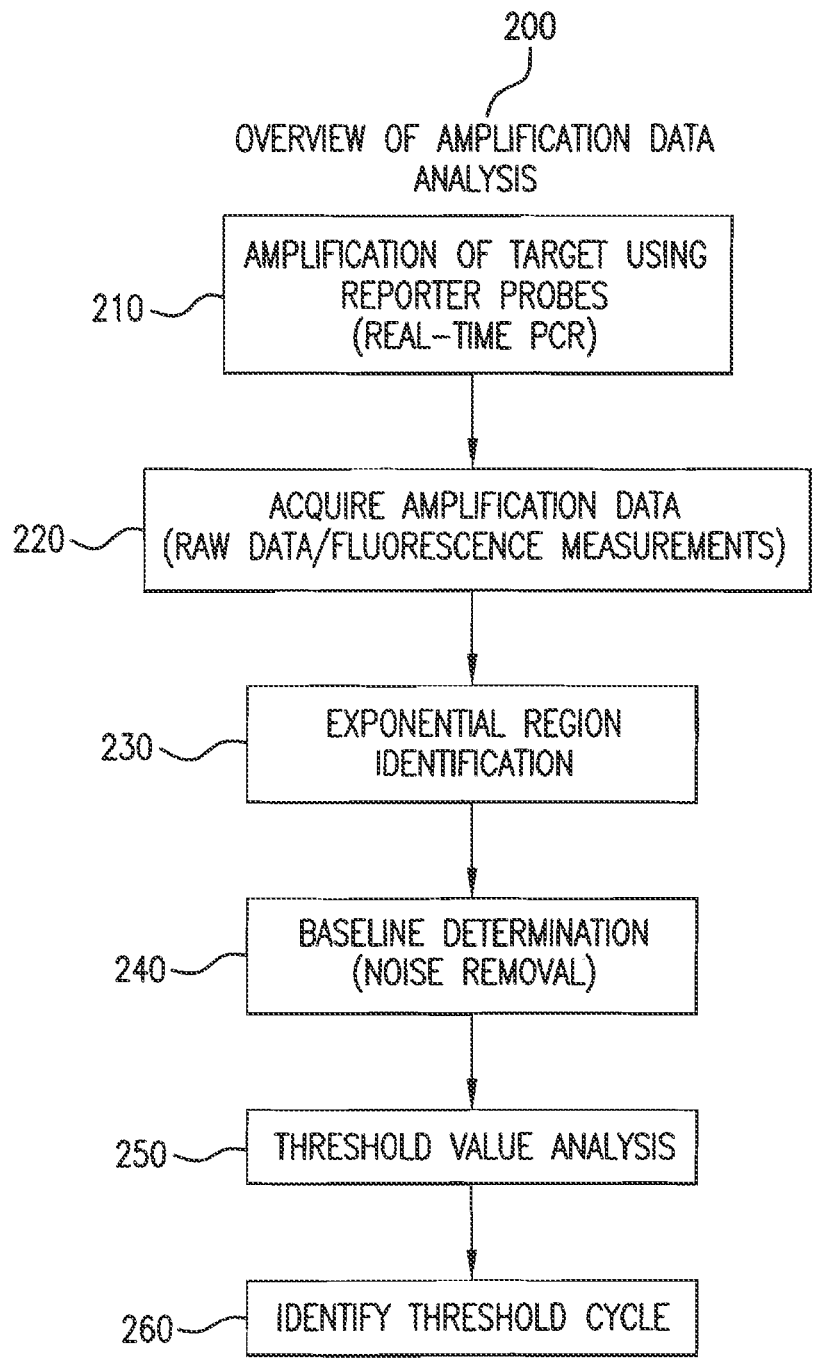
FIG. 2 is a flowchart illustrating an overview of an amplification data analysis method.

FIG. 2 illustrates one embodiment of a method 200 that may be used to analyze amplification data to provide information which is useful in performing quantitation calculations. In one aspect, the method may be adapted to operate in real-time PCR processes wherein quantitation calculations are performed using intensity data collected at various times throughout the course of an amplification reaction. It will be appreciated, however, that this method may be adapted to other types of amplification reactions and is therefore not limited exclusively to analysis of data in real-time or quantitative PCR.

The method 200 commences in state 210 with the amplification of a target in the PCR reaction. As previously described, during amplification, a reporter construct or probe may be incorporated into the contents of the reaction to provide a means for monitoring the reaction progression. In one aspect, the reporter construct comprises a probe that fluoresces in relative proportion to the quantity of progeny molecules synthesized during the amplification reaction.

During amplification of the target, intensity data or fluorescence measurements are acquired in state 220. Typically, the intensity measurements are made over a selected number of sampling intervals which allow the progression of the amplification reaction to be monitored and assessed. In various embodiments, the sampling interval may be representative of the progression of the reaction measured as a function of cycle number or time. For example, PCR-based amplification reactions typically proceed according to pre-selected temperature-dependant programs comprising cyclic variations in temperature which occur over one or more designated time intervals. In one aspect, the number of cyclic variations in temperature for which the amplification reaction is subjected to defines the overall course of the reaction. Therefore, the amplification reaction may be conveniently subdivided according to the number of cycles used in the amplification reaction or alternatively one or more designated time intervals may be used as a means to distinguish the reaction progression.

Acquisition of intensity data or fluorescence measurements may likewise be flexibly determined. Additionally, intensity measurements may be acquired to generally coincide with the cycles of the reaction. Collectively, the acquired intensity data for the reaction define the data points 107 that reflect the amplification profile 117 characteristic of each reaction. It will be appreciated that the aforementioned manner of data acquisition based on cycle number or time is not rigidly defined and may be readily varied without departing from the scope of the invention. For the purposes of illustration and discussion, however, the intensity measurements for the amplification data are presented in terms of cycle number.

Thereafter, in state 230 the exponential region 125 of the amplification reaction is determined by identification of the region's upper and lower bounds. As will be described in greater detail herein below, the upper bound 145 is first determined through a derivatization process in which the fluorescence intensity data points are transformed so as to identify a transition point between the exponential region 125 and the plateau region 130. Thereafter, the lower bound 147 of the exponential region 125 is determined by incrementally assessing the data points 107 that fall below the identified upper bound 145.

Following, exponential region identification, the process 200 proceeds to a state 240 where a baselining operation is performed. In one aspect, the baselining operation comprises identifying the bounds of the baseline region 120 and performing a linear interpolation to identify the characteristic equation defining the baseline 123 which passes approximately through the data points 107 of the baseline region 120. The bounds of the baseline 123 can be determined, in part, by identification of the bounds of the exponential region 125. In one aspect, the identified lower bound 147 of the exponential region 125 indicates the approximate upper bound of the baseline region 120. Furthermore, the approximate lower bound of the baseline region 120 may be defined by the start cycle of the reaction or a selected number of cycles (or a designated interval) from the start cycle. In one embodiment, the lower bound of the baseline region 120 may be designated as the data point 107 corresponding to the second cycle of the amplification profile 117.

In various embodiments, the linear interpolation utilized in baseline construction comprises performing a linear regression analysis for two or more data points 107 contained within the baseline region 120 to identify the characteristic baseline equation that can be "fit" to the data points 107 of the baseline region 120. Thereafter, the baseline 123 may be extended 124 out to the terminal cycle of the amplification reaction. In one aspect, identification and extension of the baseline in this manner provides a means for determining the relative noise or non-specific fluorescence present in the intensity data. Using the baseline 123 and extended baseline 124 as a reference, the amplification data may be processed so as to substantially remove the noise component from each fluorescence data point 107 to generate a normalized data set from the original data.

Following baseline determination in state 240, the method 200 proceeds to state 250 where the threshold 135 is identified. Threshold identification may incorporate a data smoothing function as well as a polynomial equation/root identification function to define an appropriate threshold 135 and threshold cycle 140 for each amplification reaction. As will be described in greater detail herein below, the threshold identification process utilizes the upper and lower exponential region bounds 145, 147 to approximate one or more amplification profiles or curves that are fit along various portions of the exponential region.

By evaluating these curves with respect to one another, a polynomial equation can be identified that describes the characteristics of at least a portion of the profile 117. In one aspect the "real" root of the polynomial equation may be found to identify the threshold cycle 140. The threshold cycle 260 may then be used in subsequent calculations to quantitate the concentration of target present in the initial reaction.

Unlike conventional methods which subjectively assess the amplification data to identify the threshold cycle 260, various embodiments of the present invention provide a means for more rapidly and reproducibly identifying exponential and baseline regions of the amplification profile 117 to facilitate subsequent identification of the threshold 135 and threshold cycle 140. Utilizing this method 200 may further improve the accuracy and reproducibility of the analysis and reduce or eliminate the need to visually inspect the intensity data which might otherwise introduce an undesirable subjective bias into the analysis.

Furthermore, in various embodiments, the methodologies described herein may be advantageously integrated into software applications and/or computer hardware so as to perform the baseline determination in a substantially automated manner without the requirement of user intervention. This inventive feature may therefore improve the performance of PCR-based quantitation and provide more rapid identification of initial target concentrations as compared to other less efficient conventional analysis methodologies.

Figure 3A:
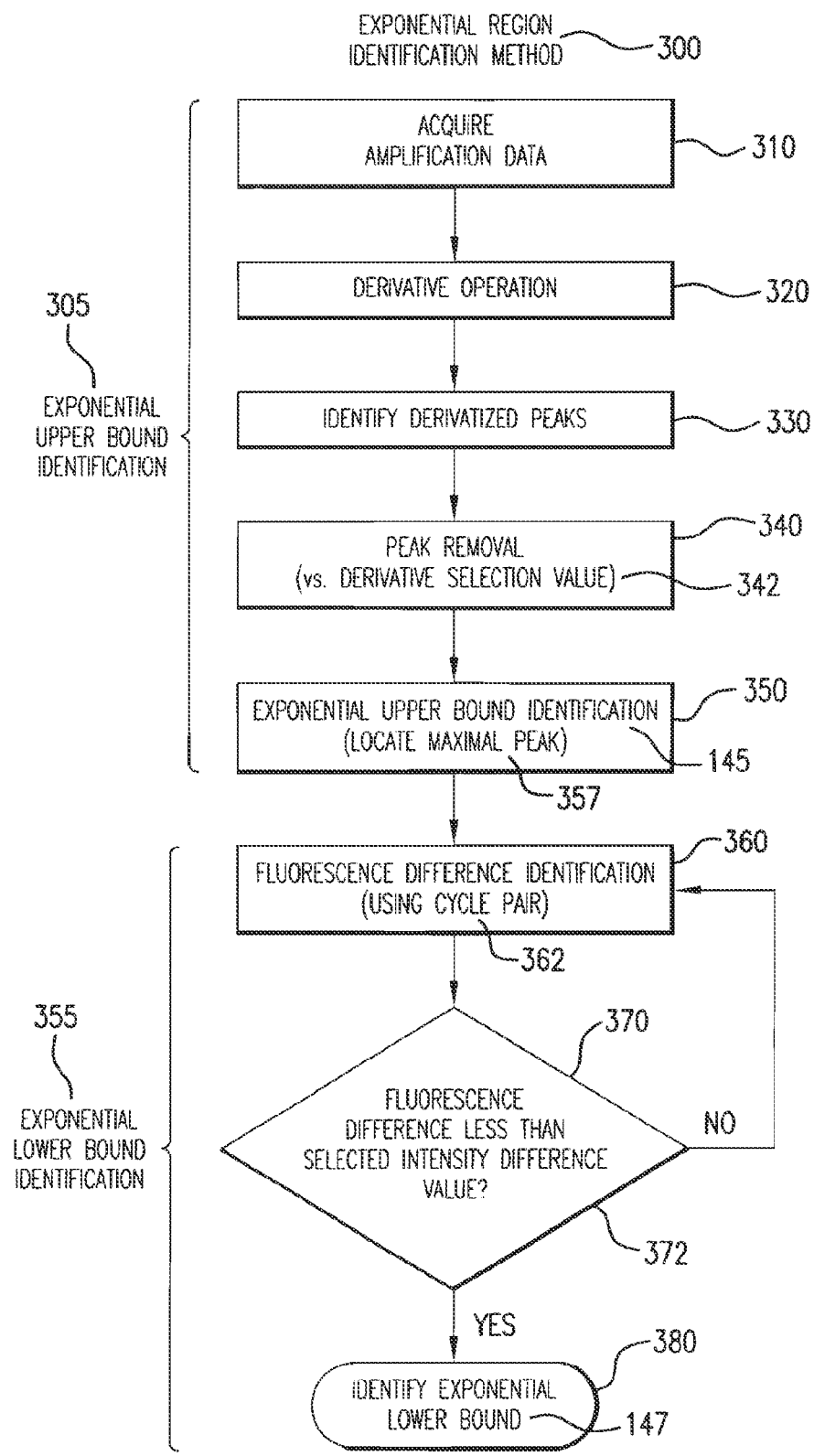
FIG. 3A is a flowchart illustrating one embodiment of a method for exponential region determination.

FIG. 3A illustrates one embodiment of a method 300 for exponential region identification. In one aspect, this method operates using a data set comprising intensity information obtained from one or more amplification reactions. Using the acquired intensity information, this method 300 desirably identifies the bounds of the exponential region 125 of the amplification profile 117. In one aspect, the exponential region identification method 300 comprises a series of steps directed towards approximating the upper bound 145 of the exponential region 125. The exponential region identification method 300 further approximates the lower bound 147 of the exponential region 125. The lower bound 147 of the exponential region 117 may additionally be used in baselining operations as will be described in greater detail in conjunction with subsequent illustrations.

The method 300 commences in state 310 with the acquisition of amplification data comprising the fluorescence information or intensity data from the amplification reaction(s). Upon acquisition of the desired intensity data, the method 300 proceeds to state 320 where a derivatization operation is performed on the intensity data associated with each amplification reaction. Derivatization of the fluorescence intensities may be conveniently used to generate new representations of the data and facilitate identification of important amplification profile characteristics. In various embodiments, the derivatization operation further comprises calculating a first and second derivative for the intensity data associated with each amplification reaction. In the context of analysis of the amplification profile, determination of the first derivative of the intensity data may be used to identify the relative length of the exponential region 125. Furthermore, determination of the second derivative of the intensity data may be used to identify the theoretical upper bound 145 for each amplification profile 117.

In one aspect, the calculated second derivative of the intensity data generates a representation of the data comprising a plurality of "peaks". Relating these peaks to the progression (cycle number) of the amplification reaction provide a means for identifying the upper bound 145 of each exponential region 125. These peaks and their corresponding values are identified in state 330 and subsequently in state 340 the values for each peak are compared against a derivative selection value 342. In various embodiments, the derivative selection value 342 represents an empirically determined value based on the characteristics of the amplification reaction and/or the instrumentation used in the analysis. For example, in real-time PCR applications using a fluorescent reporter, a derivative selection value 342 in the range of approximately 0.001 and 0.01 may be selected for use with some nucleic acid analysis instrumentation. It will be appreciated that the derivative selection value 342 need not conform to the above-indicated values and may readily be re-defined to accommodate the characteristics of other instrumentation, reaction components, and/or reaction conditions.

When comparing each peak against the derivative selection value 342 in state 340, those peaks whose value does not exceed the derivative selection value 342 may be removed from subsequent analytical steps. In one aspect, peak selection in this manner desirably defines a minimum intensity criterion for determining the exponential region 125 of the amplification profile 117. Use of the derivative selection value 342 therefore reduces the likelihood the inappropriate values will be identified as the upper and lower bounds 145, 147 of the exponential region 125. While such a selection routine is desirable for many types of analysis, it will be appreciated that the method 300 may be adapted to not require the removal of peaks below the derivative selection value 342 and thus the operations of state 340 may be optional in some embodiments of the exponential region identification method 300

In state 350, a maximal peak 357 in the derivatized amplification profile is determined. In one aspect, the maximal peak 357 is representative to the upper bound 145 of the exponential region 125 and the location where this maximal peak 357 is found may be identified by the approximate cycle number corresponding to this value. Following identification of the exponential region upper bound 145, the method 300 proceeds to a series of steps wherein the lower bound 147 of the exponential region 125 is identified 355.

Identification of the lower bound 145 of the exponential region 125 is performed in a loop-wise manner by incrementally identifying intensity differences between each cycle commencing substantially near the upper bound 145 of the exponential region 125 in state 360 and determining if the difference falls below a selected intensity difference value 372 in state 370. In one aspect, once the top of the exponential region is found, cycle differences are identified between each cycle traveling backwards towards cycle 1. At each cycle, a comparison of the ratio of the intensity at the current cycle versus the cycle ahead of it is made. If the ratio is smaller than a predetermined ratio, then the start cycle of the exponential region may be assigned to the cycle identified by this comparison. In another aspect, the intensity difference is calculated by identifying a cycle pair 362 comprising two consecutive data points 107 starting from the upper bound 145 of the exponential region 125 and proceeding towards the first cycle of the amplification reaction. The difference in intensities determined for the cycle pair 362 is then compared to the selected intensity difference value 372. If the calculated intensity difference of the cycle pair 362 does not fall below the selected intensity difference value 372, then the method 300 loops back to state 360 where a new cycle pair 362 is selected and its intensity difference determined.

The new cycle pair 362 is found by identifying a data point 107 that precedes the cycle pair 362 whose difference was previously determined and using this value in place of the maximal value in the cycle pair 362. In this manner, intensity differences between successive cycle pairs 362 are determined starting from the upper bound of the amplification region 125 until an intensity difference is calculated which is below the selected intensity difference value 372. The cycle pair 362 whose intensity difference does not exceed the selected intensity difference value 372 is identified and thereafter the lower bound 147 of the exponential region 125 is equated to the minimal intensity value of the cycle pair 362 in state 380.

In various embodiments, the aforementioned intensity difference value 372 is empirically determined and may be dependent upon characteristics of the instrumentation, reagents and/or reaction conditions in a manner similar to the derivative selection value 342 described above. Furthermore, an intensity difference value 372 in the range of approximately 0.001 and 0.01 may be selected for use with some nucleic acid analysis instrumentation.

Using the aforementioned method 300, the exponential region 125 of an amplification profile 117 may be determined without the need for subjective analysis. Additionally, this method may be readily adapted for use in software based analysis approaches to facilitate automated processing of the amplification data with little or no user intervention. Another desirable feature of this method 300 is that exponential region identification is generally reproducible and may contribute to increased accuracy in subsequent analytical processes used in the identification of the initial target concentration.

Figure 3B:
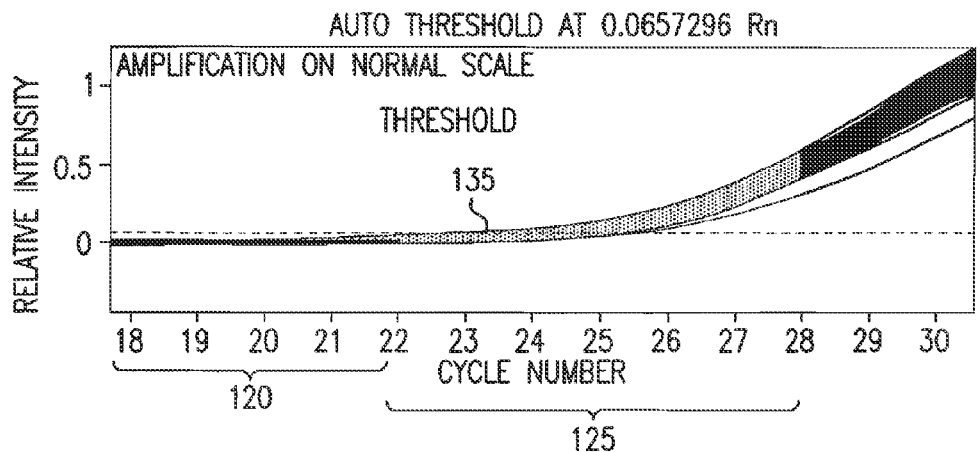
FIGS. 3B-D illustrate exemplary data analysis graphs for exponential region identification.
Figure 3C:
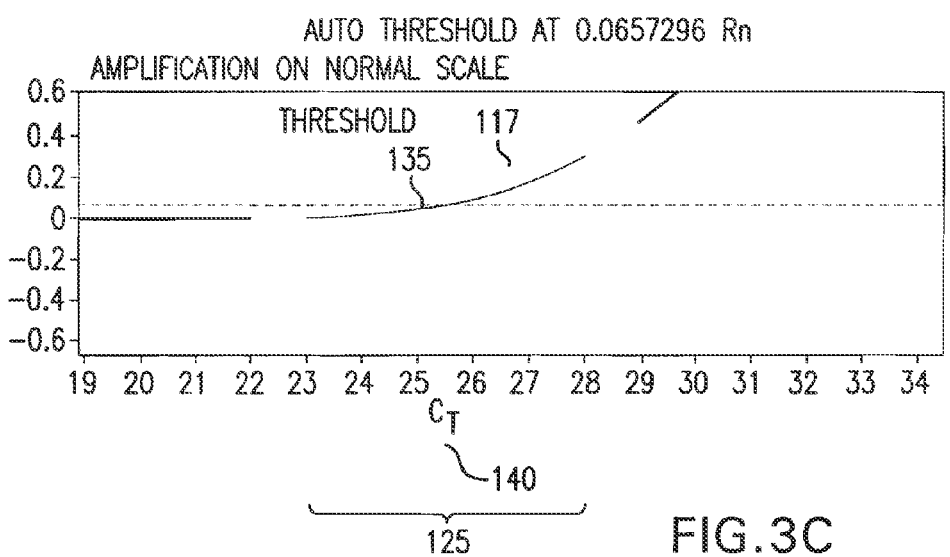
Figure 3D:
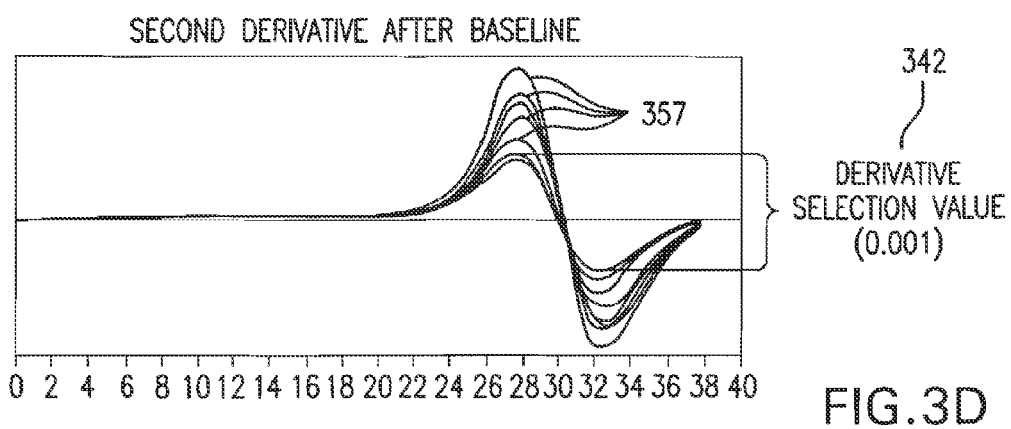

FIGS. 3B-3D illustrate the application of the exponential region identification method 300 using exemplary data shown in graphical form. It will be appreciated that the system and methods described herein do not require graphs to be generated during the analysis; however, graphical representation of the data can be performed to facilitate user visualization of the analysis and results. As such, the graphical representation of amplification data as described herein is provided for the purposes of exemplifying various features of the amplification profile that may be desirably identified during the analysis and should not be interpreted to limit the scope of the invention.

In FIG. 3B, intensity data from a plurality of amplification reactions that are to be collectively analyzed is plotted as a function of cycle number. This data reflects one embodiment of the type of information which may be collected in state 310 of the method 300. As previously described, the earlier reaction cycles may comprise a region of variability corresponding to the noise or background region 120. The background region 120 is subsequently followed by the exponential region 125 wherein the observed intensity of fluorescence in each reaction increases in a relatively exponential or geometric manner. The calculated threshold 135 for the data is further illustrated as intersecting the amplification profiles to thereby allow determination of the threshold cycle in a manner that will be described in greater detail herein below.

FIG. 3C illustrates a randomly selected amplification profile 117 from the plurality of amplification profiles shown in FIG. 2B above. The central region of the amplification profile 117 is representative of the exponential region 125 and the fractional cycle number indicated by the point of intersection between the threshold 135 and the amplification profile 117 is designated to be the threshold cycle 140. For the purposes of this illustration, the threshold cycle 140 is determined to reside between approximately cycle '25' and cycle '26'. It will be appreciated however, that the value of the threshold cycle 140 is dependent upon the data represented by the amplification profile 117 and therefore is not limited explicitly to the value indicated in the illustrated example.

FIG. 3D illustrates an exemplary representation of the intensity data graphed as a function of cycle number following the second derivative operation performed in state 320 of the method 300. Upon obtaining the second derivative for the intensity data for each of the reactions, a plurality of peaks are formed. Comparison of the peaks against the peak selection value 342 may be performed as described in state 340 of the method 300 wherein those peaks which do not exceed the peak selection value 342 are removed from subsequent analysis. In one aspect, peaks removed in this manner may represent amplification data that is not readily distinguishable from background fluorescence or noise and therefore are may not provide accurate quantitation results in subsequent analysis.

Further analysis of the peaks formed using the second derivative operation results in the identification of the maximal peak 357 for each amplification reaction as described in state 350 of the method 300. As previously indicated, the maximal peak 357 may be associated with the upper bound 145 of the exponential region 125 for a particular amplification reaction and serves as a reference point in subsequent lower bound identification 355.

Figure 4:
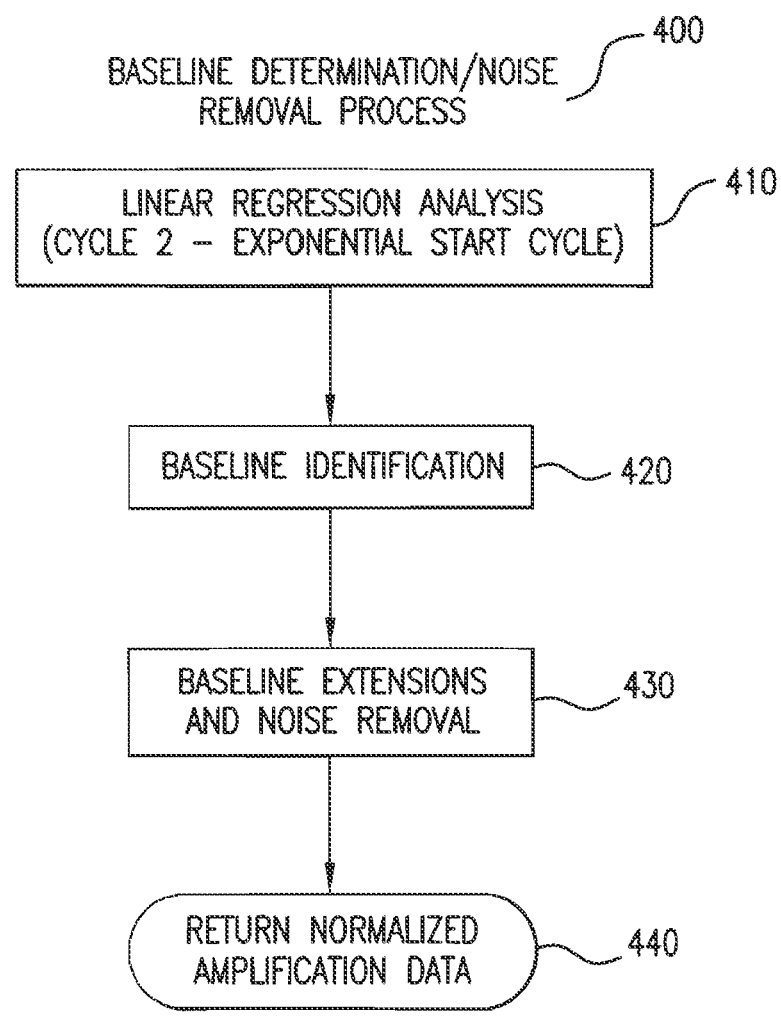
FIG. 4 is a flowchart illustrating one embodiment of a baseline determination method.

Following exponential region identification, a baseline determination method may be applied to the intensity data for each amplification reaction in the data set. FIG. 4 illustrates a method for baseline analysis 400 which utilizes the previously determined information relating to the identification of the lower bound 355 of the exponential region 125. In one aspect, this method 400 desirably approximates noise or nonspecific fluorescence present within the amplification reaction so that it may be removed from the amplification intensity data to thereby improve the quality of the quantitation. The method 400 commences in state 410 wherein a linear regression is performed on the data points 107 between the approximate beginning of the amplification reaction and the lower bound 147 of the exponential region 125. The linear regression operation serves to identify the characteristic equation that describes the baseline 123 for the amplification profile which, in one aspect, is based upon a "best-fit" approach.

In various embodiments, this method establishes the baseline 123 which corresponds to a line segment that is fit between the intensity data between the selected start cycle (typically cycle 2) and the lower bound 147 of the exponential region 125. In one aspect, the characteristic equation comprises a one-degree polynomial equation that describes the baseline 123. The characteristic equation may then be evaluated over each cycle to generate the corresponding baseline value for a particular cycle or time interval of the amplification reaction. Using this approach, the baseline 123 is extended 124 through all of the cycles of the amplification data in state 420. Baseline extension in this manner may therefore be used to approximate the amount of noise present within the data during each cycle of the amplification reaction.

In state 430, data corresponding to a normalized amplification profile is generated by subtracting the baseline value (determined from the characteristic equation) from the measured intensity data for each cycle in the amplification profile to generate the normalized amplification profile. In the normalized amplification profile, the intensity component that arises from identified noise is substantially removed. As previously described, noise may be introduced into the intensity data in a variety of manners and may include for example, instrumental noise and variabilities, background fluorescence evolved from the reagents of the amplification reaction, and other types of non-specific fluorescence that are detected by the instrumentation during data acquisition process. The data and information corresponding to the normalized amplification profile is subsequently returned in state 440 and may be used in threshold analysis as will be described in greater detail herein below.

Figure 5:
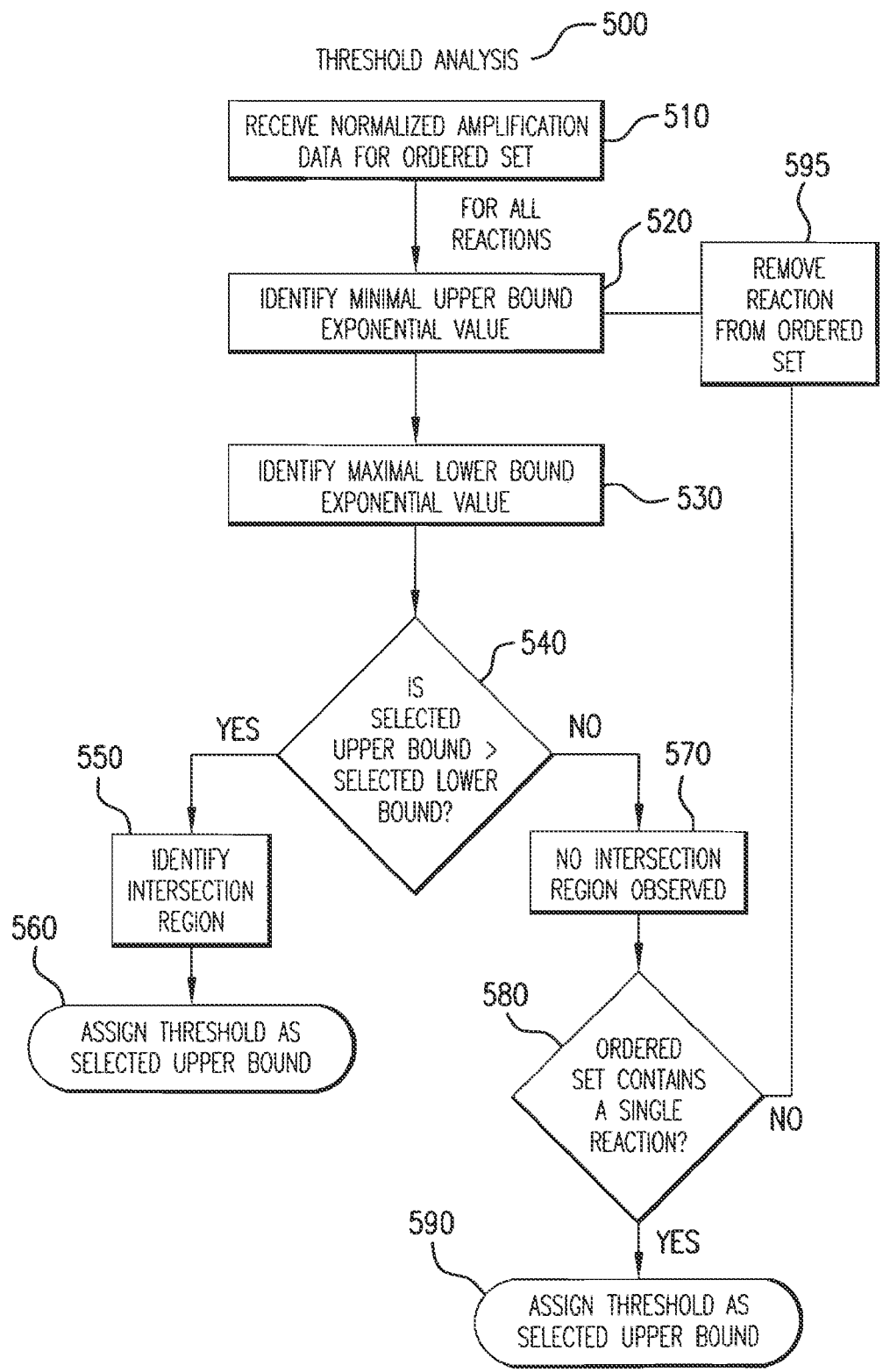
FIG. 5 is a flowchart illustrating one embodiment of a threshold determination method.

FIG. 5 illustrates one embodiment of a method for threshold analysis 500 that may be used with amplification intensity data corresponding to one or more reactions. In one aspect, this method 500 is desirably used in conjunction with amplification intensity data that has been previously normalized according to the exponential region identification and baseline determination methods 300, 400. Although the method 500 is configured for use with amplification data normalized using above the above-described methods 300, 400, it will be appreciated that other forms of raw and normalized data may also be used with the threshold analysis process 500.

The threshold determination process 500 commences in state 510 by receiving the normalized amplification data corresponding to one or more reactions that are to be desirably analyzed as an ordered set or collection. The normalized amplification data comprises intensity information collected over a plurality of cycles for each amplification reaction, as well as information regarding the upper and lower bounds of each amplification profile 117. In state 520, a minimal amplification reaction having the smallest exponential region upper bound is identified from the ordered set. Furthermore, in state 530, an maximal amplification reaction having the largest exponential region tower bound is identified from the ordered set.

Subsequently, in state 540 a comparison is made between the values of the identified upper and lower bounds 145, 147. If the results of this comparison indicate that the smallest identified upper bound is larger than the largest identified lower bound then the method 500 proceeds to state 550 indicating that an intersection region is observed. From this determination, in state 560 the threshold 135 is assigned as the value of the smallest identified upper bound of the ordered set.

Otherwise, in state 540 if the results of the comparison between the values of the identified upper and lower bounds indicate that the smallest identified upper bound is smaller than the largest identified lower bound then the method 500 proceeds to state 570 indicating that no intersection region is observed in the current iteration. In state 580, if the current number of amplification reactions in the ordered set correspond to a single amplification reaction then the method 500 proceeds to state 590 where the threshold 135 is assigned as the upper bound of the exponential region of the remaining amplification reaction. Alternatively, if more than one amplification reaction resides in the ordered set, then the method 500 proceeds to state 595 where the minimal amplification reaction is removed from the ordered set and thereafter the method proceeds to state 520 where a new minimal amplification reaction is selected. The newly selected minimal amplification reaction corresponds to the reaction whose lower bound exceeds that of the other reactions within the ordered set (from which the former minimal amplification reaction has been removed). Thereafter, the method 500 proceeds as before, resulting in the comparison between the values of the newly identified upper and lower bounds. This process continues until a threshold 135 has been assigned in either state 560 or state 590. Additional details of the threshold determination process will be described in reference to FIG. 7 (below).

Figure 6:
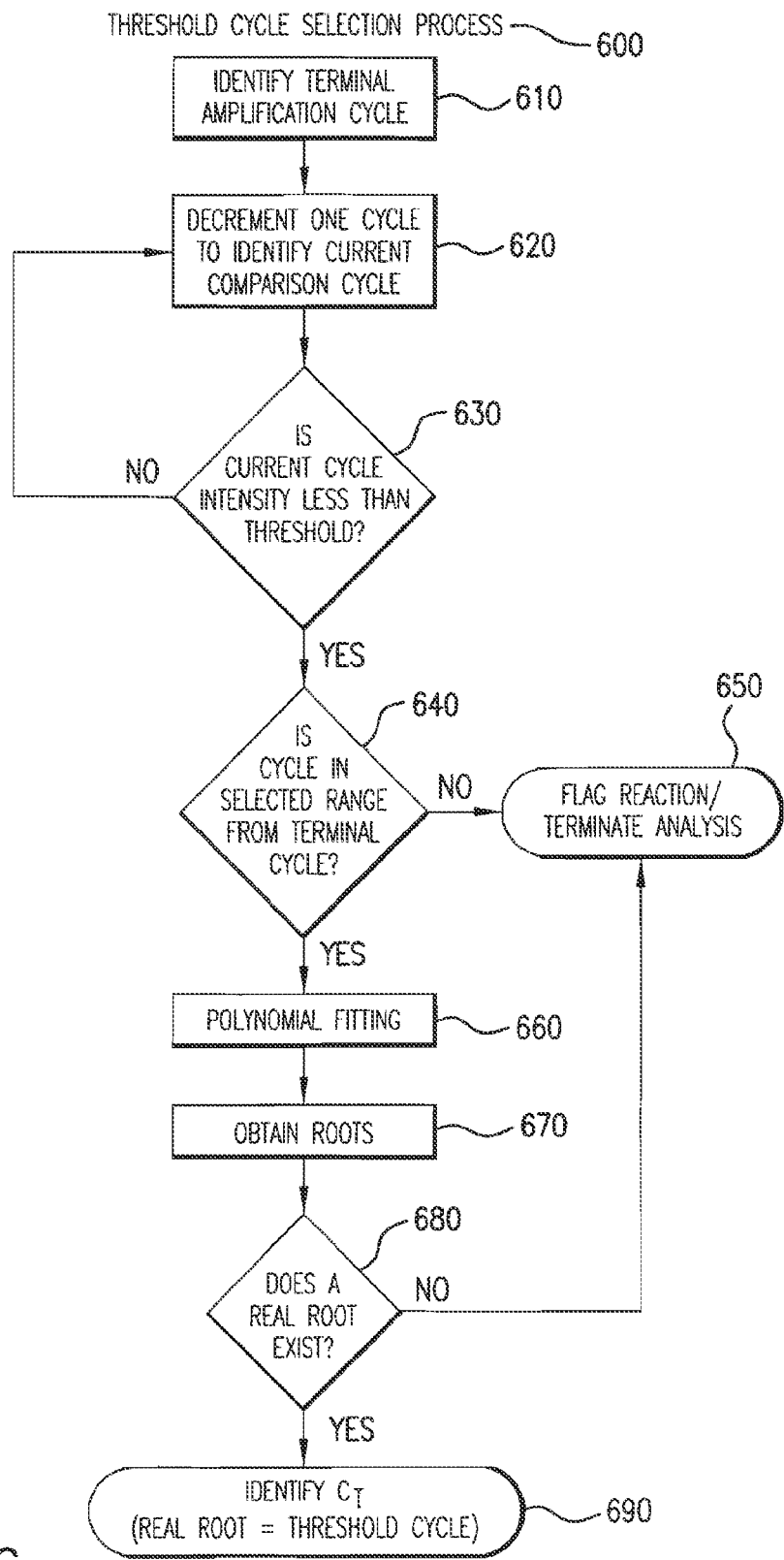
FIG. 6 is a flowchart illustrating one embodiment of a threshold cycle selection method.

FIG. 6 illustrates one embodiment of a threshold cycle selection process 600 that may be used for determining the threshold cycle ($C_T$) 140. In one aspect, the method 600 utilizes the threshold 135 previously determined in threshold analysis procedure 500 described in conjunction with FIG. 5 above. The method 600 commences in state 610 where a terminal cycle is identified. The terminal cycle is typically selected as the endpoint of the amplification reaction (cycle 40 in the illustrated amplification plot shown in FIG. 1), however, it will be appreciated that designation of the terminal cycle may be substantially any value within the plateau region 130 or the exponential region 124 of the amplification profile 117. In state 610, a current comparison cycle is selected by decrementing one cycle from the terminal cycle. The fluorescence intensity value of the current comparison cycle is then compared to the value of the threshold 135 in state 630.

If the current comparison cycle is determined to be greater than the threshold 135 then the method 600 loops back to state 620 where the cycle is again decremented to determine the next current comparison cycle. In this manner, the method 600 incrementally compares each data point 107 with the threshold 135 until a data threshold point is found having an intensity less than the threshold 135. The method 600 then proceeds to state 640 where a determination is made as to the position of the data threshold point within the amplification profile 117. In one aspect, this state 640 verifies that the threshold data point falls within an acceptable range of the amplification profile 117. Here a range validation operation may be performed which comprises determining if the threshold data point resides within a selected range from the terminal PCR cycle. In one aspect, the selected range may be determined by assessing if the threshold data point is greater than a minimum cycle number (for example greater than a minimum cycle number of 3, 4, 5, 6, or 7) and furthermore if the threshold data point is less than a selected number of cycles away from the terminal PCR cycle (for example less than 3, 4, 5, 6, or 7 cycles away from the terminal cycle).

The range determination and verification made in state 640 helps avoid anomalous data points, which might otherwise lead to potentially inaccurate quantitation results. If the threshold data point is determined not to meet the criteria set forth in state 640 then the method 600 proceeds to state 650 where the analysis is terminated for the particular amplification reaction undergoing analysis. In one aspect, if the intensity data for the amplification reaction does not meet these criteria then the resulting amplification profile 117 is considered suspect and the reaction is flagged as potentially anomalous or erroneous. In this manner, the method 600 may identify anomalous amplification reactions whose confidence level for accurate quantitation is diminished based on the characteristics of the intensity data.

In one aspect, the value of the minimum cycle number and the value of the selected cycle number away from the terminal cycle are empirically determined. For certain instrumentation and reaction compositions, the minimum cycle number may be selected to correspond to a cycle number between approximately 3-7 which is desirably selected in combination with a selected cycle number of approximately 3-7 cycles from the terminal PCR cycle.

If the threshold data point passes the aforementioned criteria set forth in state 640, then the method 600 proceeds to state 660 where a polynomial fitting procedure is implemented to find an equation which can be fit to the amplification reaction data. In one aspect, the polynomial fitting procedure comprises identifying a polynomial equation which starts a predetermined number of cycles above and below where the threshold data point was selected in state 640 above. For example, in one implementation, upon identifying the threshold data point in state 640, a 3rd degree polynomial is fit over the amplification reaction data starting a selected number of cycles above and below where the data point 107 was identified.

It will be appreciated that the polynomial equation that is fit to the amplification profile may be of varying degrees and need not necessarily be limited exclusively to a 3rd degree polynomial. Additionally, the position at which the polynomial equation is fit to the amplification profile may be similarly varied and therefore need not necessarily be limited exclusively to a fixed number of cycles above and below the threshold data point identified in state 640. In general, the polynomial fitting operations serve to smooth the data in the locality of the threshold data point. In one aspect, the polynomial fitting operations comprise an implementation of the Savitzky-Golay method for smoothing. Details of this method are described in detail in Numerical Recipes, Press et al. 1992.

Following polynomial fitting in state 660, the method 600 proceeds to state 670 where the threshold 135 is subtracted from the constant portion of the polynomial equation (i.e. the Y-intersection coefficient) and the roots of the polynomial are determined. Based on the identified roots of the polynomial equation, a determination is made as to whether or not a real root for the polynomial equation exists in state 680. If no real root exists, the method proceeds to state 650 where the analysis is terminated for the amplification reaction and the reaction data flagged to indicate a possible anomalous or erroneous reaction. If however, the real root is determined to exist in state 680, then the method proceeds to state 690 where the real root is associated with the threshold cycle ($C_T$) 140 for the amplification reaction under analysis.

Using the threshold cycle 140 identified using the method 600 described above, conventional quantitation procedures may be used to determine the initial concentration of target present in the amplification reaction. For example, in various embodiments the threshold cycle ($C_T$) 140 may be defined as a cycle or fractional cycle number at which the observed fluorescence intensity data of the amplification reaction passes the identified threshold 135. Furthermore, quantitation of the amount of target in a sample may be accomplished by measuring the threshold cycle 140 and using a standard curve constructed from reactions having known target concentrations to determine the starting concentration or copy number of the experimental target. It will be appreciated that the aforementioned methods advantageously perform the threshold cycle determination with little or no required user input or decision making. As a result, subjective variability in the quantitative analysis of PCR-based amplification data may be substantially removed. Furthermore, as previously described, analysis of the amplification data in the aforementioned manner may advantageously improve the degree of accuracy and reproducibility of the experimental analysis, as well as identify anomalous or erroneous amplification reactions which might otherwise lead to inaccurate quantitation results.

Figure 7A:
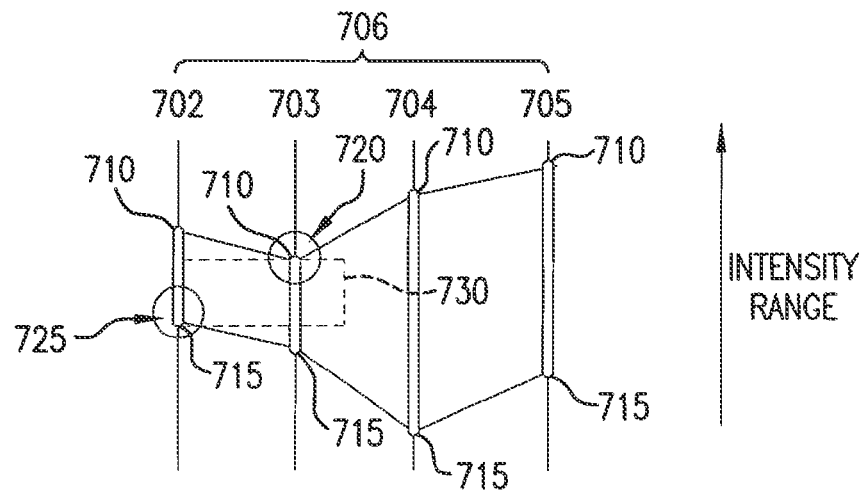
FIGS. 7A-D are diagrams illustrating the threshold cycle selection method applied to a plurality of amplification profiles.

FIGS. 7A-D further illustrates one embodiment of the aforementioned methods for threshold determination wherein a plurality of amplification curves or profiles 702-705 are analyzed as a single ordered set 706. In FIG. 7A, the plurality of amplification profiles 702-705 corresponding to predicted exponential regions are shown as vertical lines. Each amplification profile 702-705 comprises an upper bound 710 and a lower bound 715. The bounds 710, 715 for each amplification profile 702-705 are determined according to the exponential region identification method 300 (shown in FIG. 3A). Proceeding through the threshold analysis 500 (shown in FIG. 5), the method 500 first collectively evaluates the upper bounds 710 for the amplification profiles 702-705. From this assessment, the smallest upper bound 720 of the ordered set 706 is identified. In a similar manner, the lower bounds 715 for the amplification profiles 702-705 are collectively evaluated to determine the highest lower bound 725 for the ordered set 706.

Figure 7B:
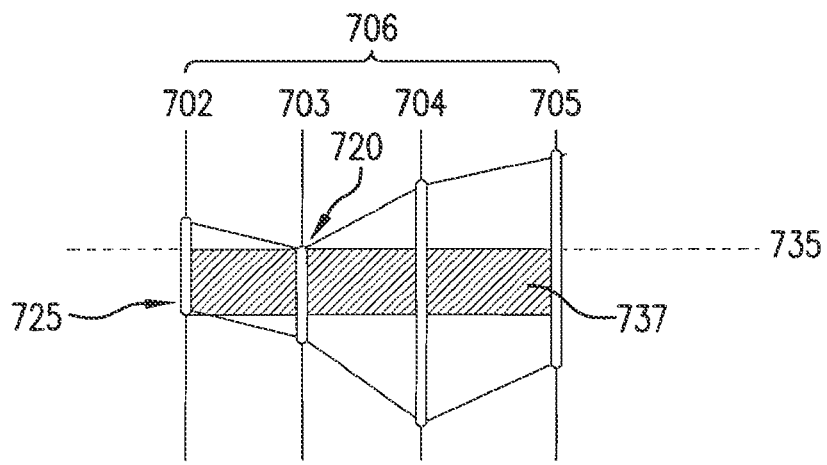

If the smallest upper bound 720 is determined to be greater in magnitude or intensity than the largest lower bound 725 then art intersection 730 between the amplification profiles 702-705 is determined to exist. In this instance, the threshold 735 is assigned to the greater of the two limits corresponding to the smallest identified upper bound 720, as shown in FIG. 7B. Additionally, the threshold 135 delineates the upper bound of a threshold region 737 which is further bounded by the largest lower bound 725.

The threshold cycle ($C_T$) may then be determined by evaluating the cycle at which the threshold 735 intersects with the amplification profiles 702-705 of the ordered set 706. As previously described, this method of threshold cycle determination may be readily automated and does not require significant user interpretation or assessment.

Figure 7C:
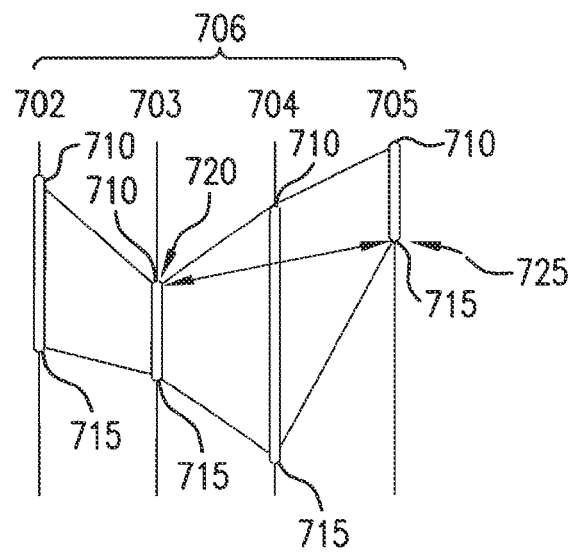

FIG. 7C illustrates the occurrence when an intersection point is not found between the amplification profiles 702-705 of the ordered set 706. In this instance, the lowest upper bound 720 does not intersect with the highest lower bound 725. Accordingly, as described in the threshold analysis method 500, amplification profiles are incrementally discarded until intersection criteria are met.

Figure 7D:
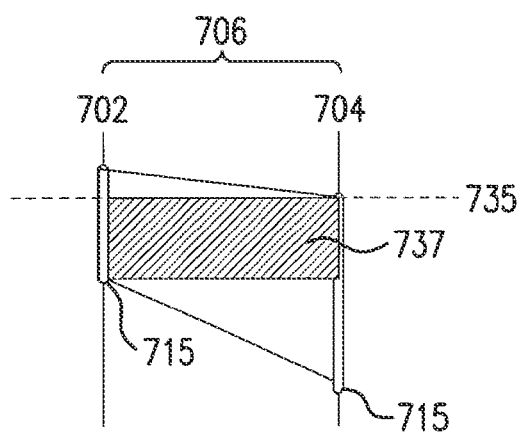

As shown in FIG. 7D, applying the intersection criteria to the amplification profiles 703-705 illustrated in FIG. 7C results in the discarding of two amplification profiles 703, 705 from the ordered set 706. Of the remaining amplification profiles 703, 705, an intersection point between the lowest upper bound 720 and the highest lower bound 725 can be obtained which is designated as the threshold 135. Following threshold identification, an intersection region can be observed similar to that found in FIG. 7B above. Using this information, the threshold cycle is likewise obtained and subsequently used in quantitation calculations.

It will be appreciated that the threshold 735 assignment may be determined in a number of different ways upon identification of the intersection region 730 and is therefore not limited solely to assignment as the smallest upper bound 720. For example, in another embodiment, the threshold 735 may be assigned to the highest lower bound 725. Alternatively, the threshold 735 may be assigned to a value midway between the bounds 720, 725. In these and other embodiments, the assigned threshold 135 functions in substantially the same manner as the above-described threshold assignment method. Taken together, these methods of threshold assignment provide a degree of flexibility wherein the value of the threshold 735 may be varied based upon a desired assignment criteria to yield different stringencies for determining the threshold cycle ($C_T$).

Figure 8:
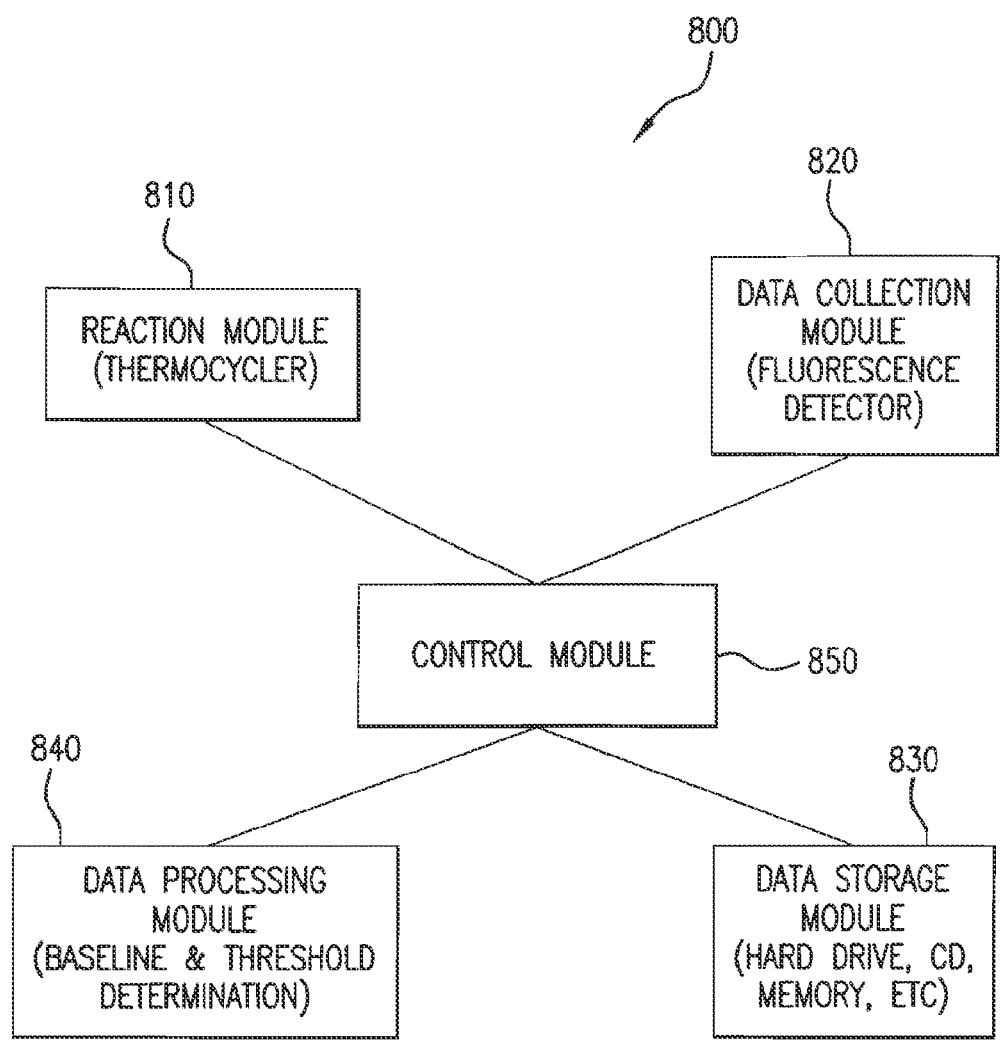
FIG. 8 is a block diagram of a quantitative PCR system incorporating an automated threshold detection module.

FIG. 8 illustrates a system 800, according to various embodiments, for performing quantitative PCR in conjunction with the aforementioned baseline and threshold analysis methodologies. In one aspect, the system 800 comprises a plurality of modules interconnected or networked by way of a communications medium to substantially automate the analysis. A reaction module 810 receives the samples to undergo amplification and provides the necessary hardware to regulate the temperature of the samples in a desired manner. For example, reaction module 810 may comprise a thermocycler or other hardware device capable of being programmed with a particular method which defines controlled heating and cooling steps executed over designated time intervals.

The system 800 further comprises, in various embodiments, a data collection module 820 that detects and measures the fluorescence generated for each amplification reaction. The data collection module 820 may be configured to read the fluorescence directly while the reaction module 810 is in operation or alternatively samples from the amplification reactions may be withdrawn and measured separately by the data collection module 820. In one aspect, the data collection module 820 comprises a fluorescence detector configured to measure fluorescence at the emission wavelength for a particular label or reporter incorporated into the amplification reaction.

The data collection module 820, according to various embodiments, can transmit the fluorescence data to a data storage module 830 responsible for archiving the fluorescence results for each reaction over the specified time course. The data storage module 830 may store the data in numerous different forms and configurations including tables, charts, arrays, spreadsheets, databases, and the like. In one aspect, the data storage module 830 receives the results from many different experiments and presents the data to other modules responsible for the subsequent comparison and analysis of the data. Furthermore, the data storage module 830 stores the results of the quantitation analysis which may be output as needed or requested.

A data processing module 840, according to various embodiments, receives selected data from the data storage module 830 or alternatively from the data collection module 820 and performs the operations associated with noise determination and threshold selection. These analytical methods may be implemented using one or more computer program or modules which comprise functions designed to manipulate the data and generate requested information including: baseline noise level determination, exponential region identification, threshold selection and combination, quantitative analysis, and other related analytical methods. In one aspect, the data processing module 840 is designed to operate in a user-independent manner where all of the calculations and analytical tasks are performed without the need for the user to manually assess or interpret the data.

Finally, in certain embodiments, a control module 850 may be incorporated into the system 800 to provide a means for integrating the tasks associated with each module. The control module 850 may be configured to communicate with each module of the system 800 and coordinates system-wide activities to facilitate the automated quantitative PCR analysis. Additionally, the control module 830 may monitor each module to verify their proper function and provide a user interface for interacting with the various components of the system 800.

Figure 9:
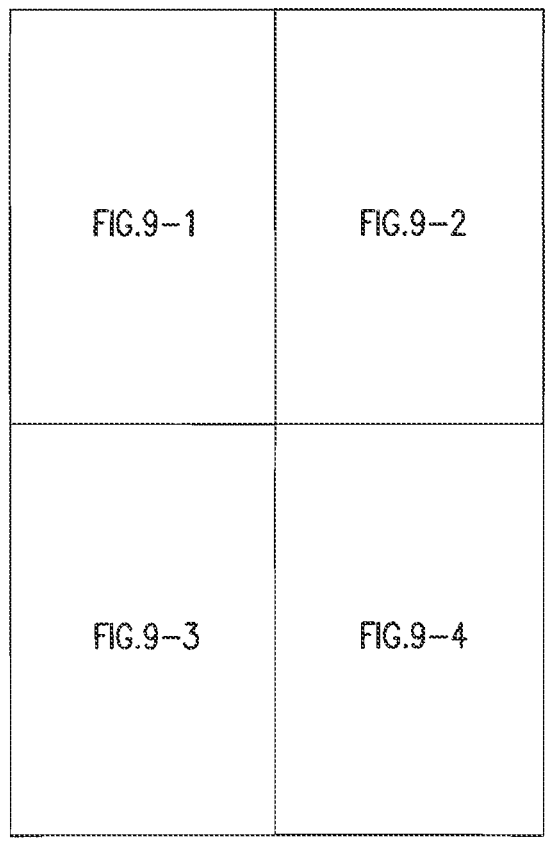
FIG. 9 is an exemplary pseudo-code implementation of the threshold and threshold cycle identification methods.
Figures 1, 9:
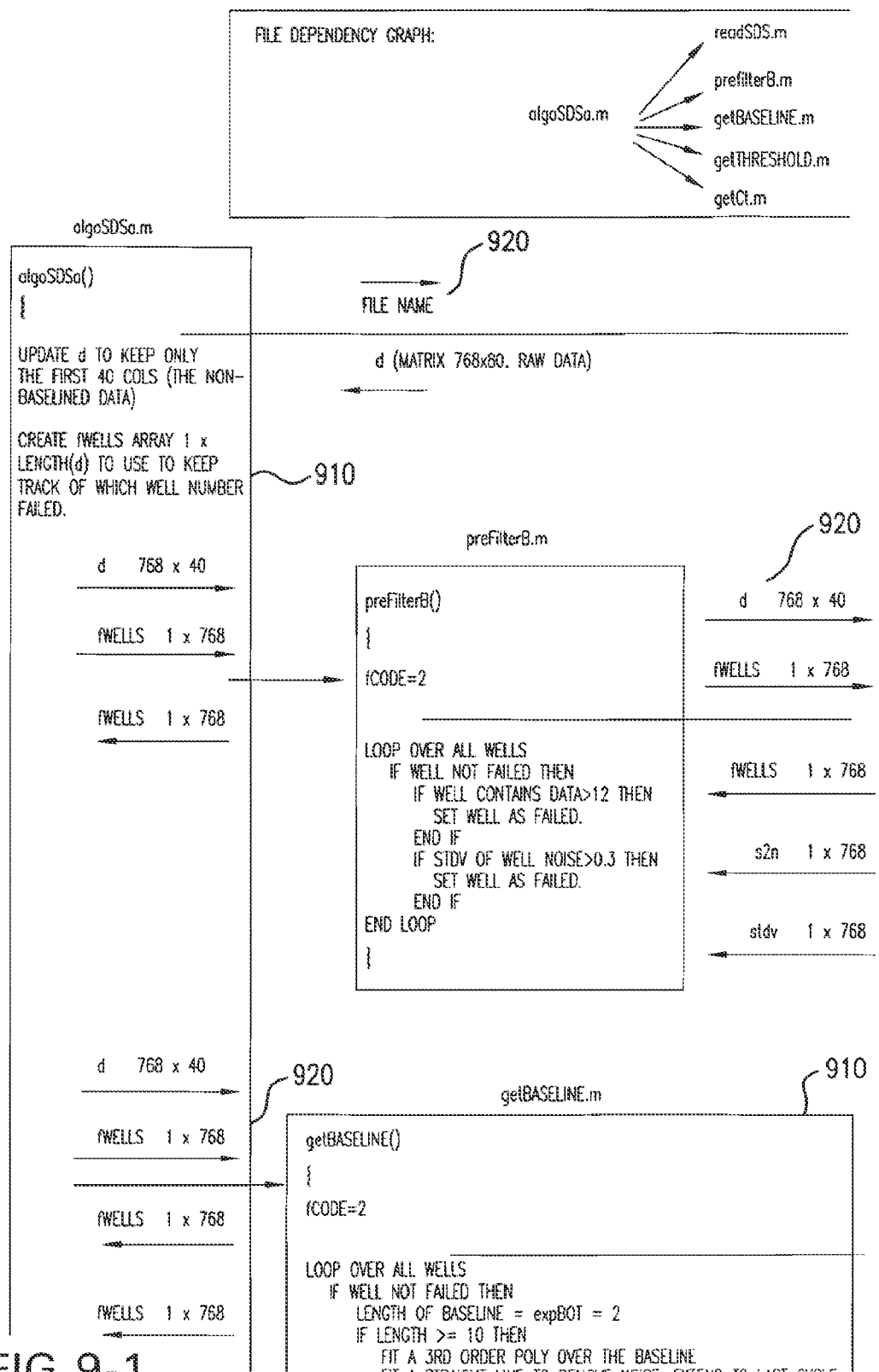
Figures 2, 9:
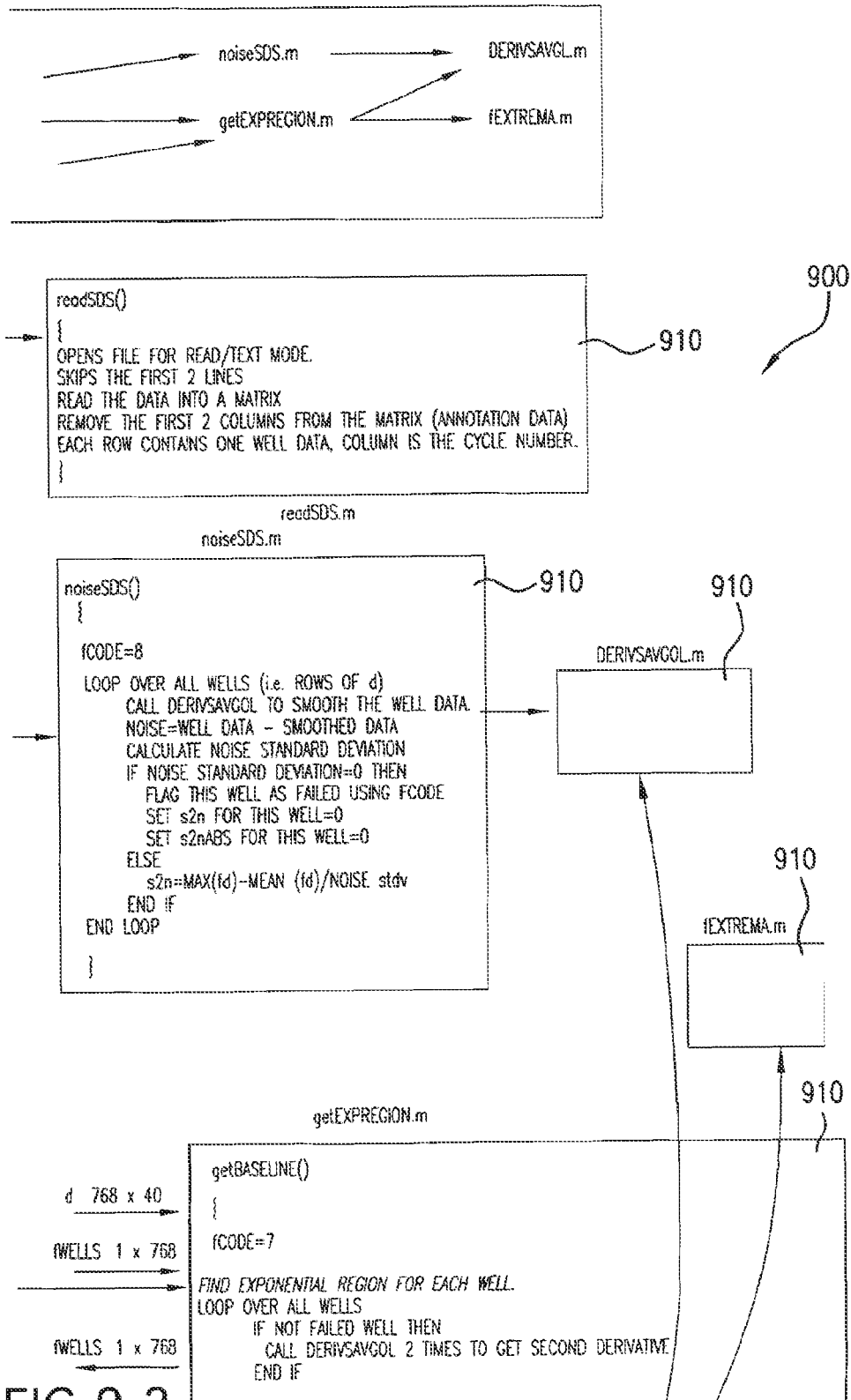
Figures 3, 9:
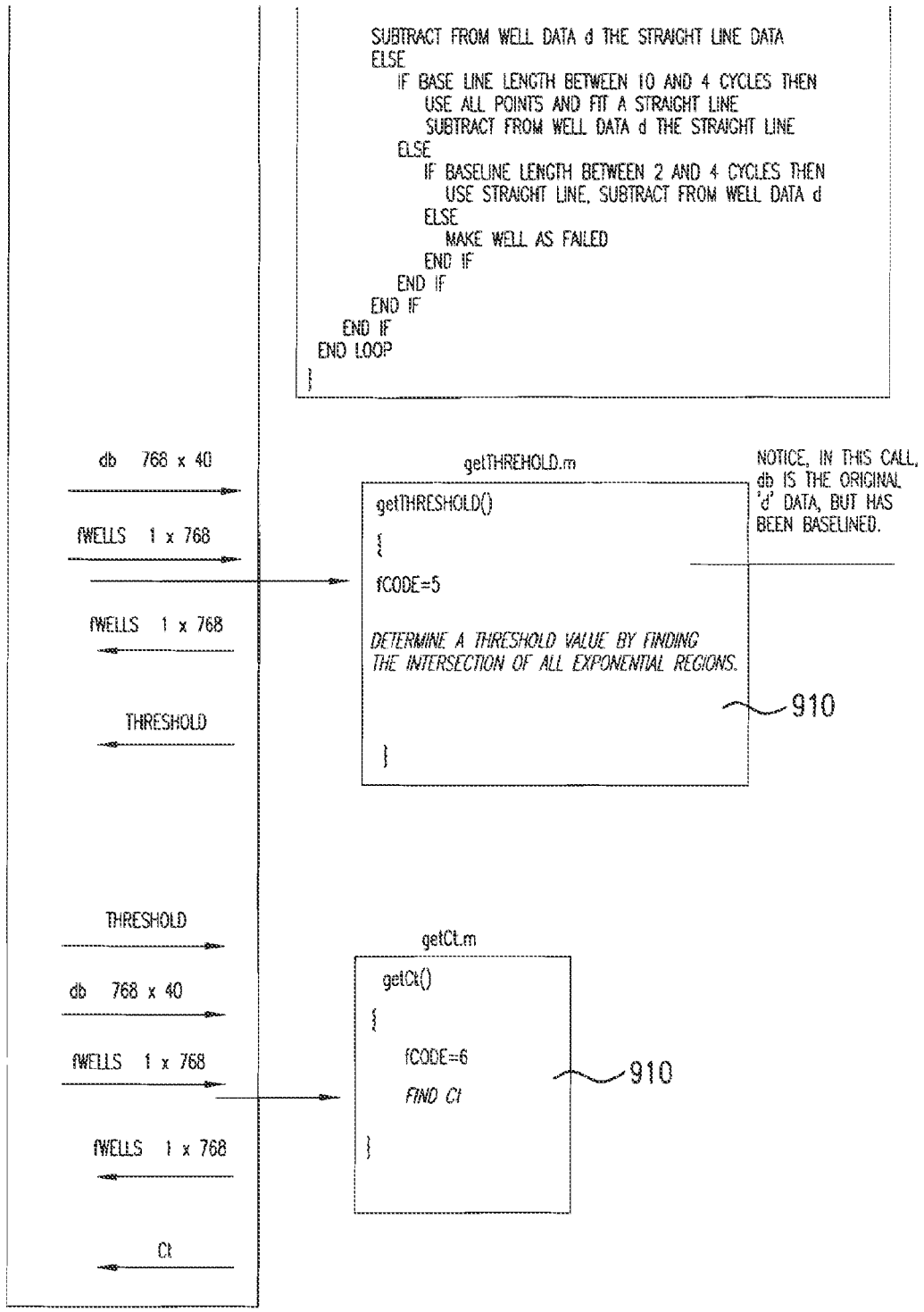
Figures 4, 9:
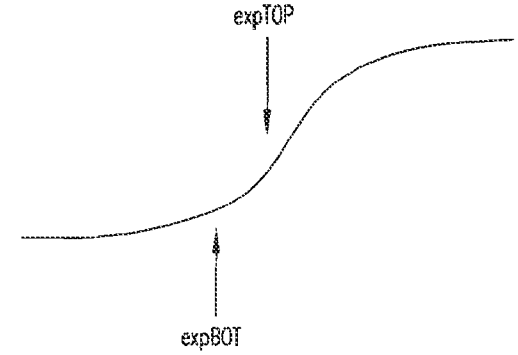

FIG. 9 illustrates an exemplary code construction 900 comprising pseudo-code for various functions related to the determination of the threshold 135 and threshold cycle 140. In one aspect, a plurality of modules 910 are used to perform the threshold 135 and threshold cycle 140 identification operations which pass data and parameters 920 between one another to coordinate the calculations. It will be appreciated that the illustrated code construction 900 represents but one embodiment of how the aforementioned methods may be implemented and other programmatic schemas may be readily utilized to achieve similar results. As such, these alternative schemas are considered to be but other embodiments of the present invention.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A method for target sequence quantitation, comprising:
amplifying a plurality of target sequences by PCR in the presence of a detectable reporter construct;
acquiring signal information for each target sequence of the plurality of target sequences amplified by detecting the associated detectable reporter construct;
identifying a plurality of exponential regions, wherein each exponential region is associated with substantial increases in the signal information for each target sequence amplification and wherein each identified exponential region comprises an associated upper and lower bound;
normalizing the signal information for each target sequence amplification using an identified baseline component for the signal information to compensate for non-specific fluorescence in the signal information;
determining an exponential region threshold based on a comparison of the plurality of exponential regions, wherein each exponential region of the plurality of exponential regions is associated with a target sequence amplification of the plurality of target sequence amplifications;
performing a fitting operation to at least an interval of the exponential region including the exponential region threshold;
identifying, based on the exponential region threshold and an associated polynomial root, a threshold cycle for the at least one target sequence amplification.

2. The method of claim 1, wherein identification of the exponential region upper bound comprises performing a derivative operation.

3. The method of claim 2, wherein the derivative operation comprises obtaining a second derivative using the signal information.

4. The method of claim 3, wherein the identification of the exponential region lower bound comprises detecting incremental differences in the signal information starting at the exponential region upper bound.

5. The method of claim 4, wherein the incremental differences comprise at least one of differences in a ratio of detected intensity of successive values of the signal information and differences in detected intensity of successive values of the signal information.

6. The method of claim 1, wherein the normalizing comprises:
identifying a baseline region based on the exponential region lower bound;
performing a regression analysis of the baseline region to generate a characteristic equation; and
differencing the baseline component using the characteristic equation to normalize the signal information.

7. The method of claim 1, wherein the fitting operation is a polynomial fitting operation.

8. The method of claim 7, wherein the polynomial fitting operation comprises:
performing a polynomial fitting operation over a selected number of cycles including the threshold cycle to identify a threshold equation;
factoring the threshold equation to identify a real root of the threshold equation; and
associating the real root with the threshold cycle.

9. The method of claim 8, wherein the polynomial fitting operation comprises applying a Savitzky-Golay smoothing operation.

10. A system for target sequence quantitation, comprising:
a data collection module configured to collect signal information including detected reporter label intensities generated by amplifying a plurality of target sequences in the presence of a detectable reporter construct; and
a data processing module configured to:
identify a plurality of exponential regions, wherein each exponential region is associated with substantial increases in the signal information for the at least one target sequence amplification, and each exponential region comprising an upper bound and a lower bound,
normalize the signal information for each target sequence amplification using an identified baseline component for the signal information to compensate for non-specific fluorescence in the signal information,
determine an exponential region threshold based on a comparison of the plurality of exponential regions, wherein each exponential region of the plurality of exponential regions is associated with a target sequence amplification of the plurality of target sequence amplifications,
perform a fitting operation to fit a polynomial to at least an interval of the exponential region including the exponential region threshold, and
identify, based on the exponential region threshold and an associated polynomial root, a threshold cycle for the at least one target sequence amplification.

11. The system of claim 10, wherein to identify the plurality of exponential regions, the data processing module is further configured to perform-a derivative operation.

12. The system of claim 10, wherein to normalize, the data processing module is further configured to:
identify a baseline region based on the exponential region lower bound;
perform a regression analysis of the baseline region to generate a characteristic equation; and
difference the baseline component using the characteristic equation to normalize the signal information.

13. The system of claim 10, wherein the fitting operation is a polynomial fitting operation.

14. The system of claim 13, wherein the data processing module is further for performing a polynomial fitting operation, wherein performing the polynomial fitting operation comprises:
performing a polynomial fitting operation over a selected number of cycles including the threshold cycle to identify a threshold equation;
factoring the threshold equation to identify a real root of the threshold equation; and
associating the real root with the threshold cycle.

* * * * *